(12) United States Patent
Farha et al.

(10) Patent No.: US 11,666,637 B2
(45) Date of Patent: Jun. 6, 2023

(54) INSULIN-LOADED METAL-ORGANIC FRAMEWORKS

(71) Applicant: Northwestern University, Evanston, IL (US)

(72) Inventors: Omar K. Farha, Glenview, IL (US); Yijing Chen, Evanston, IL (US); Peng Li, Chicago, IL (US)

(73) Assignee: Northwestern University, Evanston, IL (US)

( * ) Notice: Subject to any disclaimer, the term of this patent is extended or adjusted under 35 U.S.C. 154(b) by 155 days.

(21) Appl. No.: 16/977,448

(22) PCT Filed: Mar. 7, 2019

(86) PCT No.: PCT/US2019/021117
§ 371 (c)(1),
(2) Date: Sep. 1, 2020

(87) PCT Pub. No.: WO2019/173571
PCT Pub. Date: Sep. 12, 2019

(65) Prior Publication Data
US 2021/0000924 A1 Jan. 7, 2021

Related U.S. Application Data

(60) Provisional application No. 62/640,944, filed on Mar. 9, 2018.

(51) Int. Cl.
*A61K 38/28* (2006.01)
*A61K 9/20* (2006.01)

(52) U.S. Cl.
CPC ............ *A61K 38/28* (2013.01); *A61K 9/2013* (2013.01)

(58) Field of Classification Search
CPC ............................... A61K 9/2013; A61K 38/28
See application file for complete search history.

(56) References Cited

U.S. PATENT DOCUMENTS

| | | | |
|---|---|---|---|
| 10,933,120 B2 * | 3/2021 | Vilhelmsen ............ | A61K 9/2077 |
| 2008/0305174 A1 * | 12/2008 | Gyurik ...................... | A61P 3/10 |
| | | | 514/772.3 |
| 2017/0166661 A1 | 6/2017 | Liang et al. | |
| 2018/0147284 A1 | 5/2018 | Orellana-Tavra et al. | |

FOREIGN PATENT DOCUMENTS

| WO | WO 2013/058844 A1 | 4/2013 |
|---|---|---|
| WO | WO 2017/213871 A2 | 12/2017 |

OTHER PUBLICATIONS

Giussani et al., ChemPhsyChem 11: 1757-1762,(2010).*
S. Wang et al., "General and Direct Method for Preparing Oligonucleotide-Functionalized Metal-Organic Framework Nanoparticles," *J. Am. Chem. Soc.* 2017, vol. 139, pp. 9827-9830. DOI: 10.1021/jacs.7b05633.
P. Deria et al., "Versatile functionalization of the NU-1000 platform by solvent-assisted ligand incorporation," *Chem. Commun.*, 2014, vol. 50, pp. 1965-1968.
W. Morris et al., "Nucleic Acid-Metal Organic Framework (MOF) Nanoparticle Conjugates," *J. Am. Chem. Soc.*, 2014, vol. 136, No. 20, pp. 7261-7264. DOI: 10.1021/ja503215w.
The International Search Report and Written Opinion issued in International Patent Application No. PCT/US2019/021117 dated May 9, 2019, pp. 1-9.
Y. Chen et al., "Acid-Resistant Mesoporous Metal-Organic Framework Toward Oral Insulin Delivery: Protein Encapsulation, Protection & Release," *J. Am. Chem. Soc.*, Just Accepted Manuscript, DOI: 10.1021/jacs.8b02089, Publication Date (Web): Apr. 11, 2018.
S. Wang et al., "DNA-Functionalized Metal-Organic Framework Nanoparticles for Intracellular Delivery of Proteins," *J. AM. Chem. Soc.*, pp. A-E. DOI: 10.1021/jacs.8b12705.
Horcajada, P. et al., Metal-organic frameworks as efficient materials for drug delivery, *Angew. Chem. Int. Ed. Engl.* 2006, vol. 45, pp. 5974-5978.
E.-S. Khafagy et al., "Current challenges in non-invasive insulin delivery systems: A comparative review," *Adv. Drug Deliv. Rev.* 2007, vol. 59, pp. 1521-1546.
Z. Dong et al., "Multivariate Metal-Organic Frameworks for Dialing-in the Binding and Programming the Release of Drug Molecules," *J. Am. Chem. Soc.* 2017, vol. 139, pp. 14209-14216.
J. Howarth et al., "Chemical, thermal and mechanical stabilities of metal-organic frameworks," *Nature Reviews Materials* Mar. 2016, vol. 1, Article No. 15018, pp. 1-15.
K. Liang et al., "Biomimetic Mineralization or Metal-Organic Frameworks as Protective costings tor Biomacromolecules," *Nature Communications*, Published Jun. 4, 2015, vol. 6, pp. 1-8. DOI: 10.1038/ncomms8240.
T. Islamoglu et al., "Revisiting the structural homogeneity of NU-1000, a Zr-based metal-organic framework," pp. 1-6. DOI: 10.1039/c8ce00455b.
C. Wang et al., "Metal-Organic Framework Encapsulation Preserves the Bioactivity of Protein Therapeutics," *Adv. Healthcare Mater.* 2018, pp. 1800950-1-1800950-9. DOI: 10.1002/adhm.201800950.
R. C. Huxford et al., "Metal-Organic Frameworks as Potential Drug Carriers," *Curr. Opin. Chem. Biol.* Apr. 2010, vol. 14, No. 2, pp. 262-268. DOI: 10.1016/j.cbpa.2009.12.012.
P. Horcajada et al., "Metal-Organic Frameworks in Biomedicine," *Chem. Rev.* 2012, vol. 112, pp. 1232-1268.
M. H. Teplensky et al., "Metal-Organic Frameworks Extends Drug Delivery Release," *J. Am. Chem. Soc.* 2017, vol. 139, pp. 7522-7532.

(Continued)

*Primary Examiner* — Gyan Chandra
(74) *Attorney, Agent, or Firm* — Bell & Manning, LLC

(57) ABSTRACT

Mesoporous zirconium metal-organic frameworks (MOFs) having insulin immobilized therein and methods of using the MOFs in insulin delivery are provided. The insulin-loaded metal-organic framework molecules include a porous zirconium metal-organic framework molecule and insulin molecules within pores of the porous zirconium metal-organic framework.

15 Claims, 29 Drawing Sheets
Specification includes a Sequence Listing.

(56) References Cited

OTHER PUBLICATIONS

P. Horcajada et al., "Porous metal-organic-framework nanoscale carriers as a potential platform for drug delivery and imaging," *Nature Materials* Feb. 2010, vol. 9, pp. 172-178.

J. Della Rocca et al., "Nanoscale Metal-Organic Frameworks for Biomedical Imaging and Drug Delivery," *Acc. Chem. Res.* Oct. 18, 2011, vol. 44, No. 10, pp. 957-968. DOI: 10.1021/ar200028a.

Y. Zhang et al., "Preparation and evaluation of alginate-chitosan microspheres for oral delivery of insulin," European Journal of Pharmaceutics and Biopharmaceutics 2011, vol. 77, pp. 11-19.

B. Sarmento et al., "Oral insulin delivery by means of solid lipid nanoparticles," International Journal of Nanomedicine 2007, vol. 2, No. 4, pp. 743-749.

T. C. Wang et al., "Scalable synthesis and post-modification of a mesoporous metal-organic framework called NU-1000," Nature Protocals 2016, vol. 11, No. 1, pp. 149-162.

\* cited by examiner

NU-1004

NU-1003

PCN-222

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' phosphate

<400> SEQUENCE: 1
ggtggtggtg gtggtggtgg tggtggtggt                                    30

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Tamra-dT
<220> FEATURE:
<223> OTHER INFORMATION: 3' phosphate

<400> SEQUENCE: 2
tggtggtggt ggtggtggtg gtggtggtgg t                                  31
```

INSULIN-LOADED METAL-ORGANIC FRAMEWORKS

CROSS-REFERENCE TO RELATED APPLICATIONS

This application is a National Stage of International Application No. PCT/US19/21117, filed Mar. 7, 2019, which claims the benefit of United States Patent Application No. 62/640,944, filed Mar. 9, 2018, the contents of which are herein incorporated by reference.

SEQUENCE LISTING

The instant application contains a Sequence Listing which has been submitted electronically in ASCII format and is hereby incorporated by reference in its entirety. Said ASCII copy, created on Mar. 10, 2023, is named 00100-0135-US_SL.txt and is 912 bytes in size.

BACKGROUND

Diabetes is a chronic metabolic disease that leads to long-term organ damage, and in some cases, death. Diabetes causes those affected to have excessive glucose content in their bloodstream. Insulin, a hormone produced by the pancreas, is responsible for regulating the concentration of glucose in blood plasma. Direct insulin injection remains the only effective therapeutic treatment for insulin resistant (IR) patients, even though several therapeutics have been designed to treat type I (T1DM) and type II (T2DM) diabetes mellitus. The development of oral insulin delivery methods is therefore necessary to reduce the pain and inconvenience inflicted on patients who must routinely receive insulin subcutaneously by injection.

Advancements in developing an oral insulin delivery agent have been hindered by challenges arising from the instability of insulin in the stomach environment. In the gastrointestinal tract, insulin is degraded by proteolytic enzymes meaning that only minimal transport of insulin across the intestinal epithelium into the bloodstream can occur. In this degradation process, the disulfide bonds in insulin are first cleaved by gastric acid, the fluid in the stomach composed of HCl and NaCl, initiating denaturation. The unfolded insulin chains are then broken into short multipeptide segments by pepsin, a digestive enzyme.

Ongoing efforts dedicated to developing oral insulin delivery agents aim to achieve high loading capacities while stabilizing the protein against degradation and controlling insulin release.

Encapsulation in biocompatible nanocarriers is recognized as a promising strategy for oral insulin delivery because particles of this size can facilitate paracellular or transcellular transport of insulin across the intestinal mucosa. To this end, various materials, such as alginate beads, nanoparticles, poly-nanocapsules, and collagen, have been examined as insulin encapsulation and delivery agents: however, due to their low porosity, these materials exhibit moderate insulin loading capacities. To achieve the desired insulin concentration (100 IU/mL) with these materials, an excess amount of the support material would be required. Further, the current strategy for increasing insulin loading requires the incorporation of adsorption enhancers like bile salts, fatty acids, and surfactants; however, this increases the concentration of undesirable molecules inside the carriers. Therefore, development of a carrier with high insulin capacity is imperative to make oral insulin delivery feasible.

Metal-organic frameworks (MOFs) are crystalline porous materials composed of metal nodes connected by organic ligands. (See, for example, Islamoglu, T., et al., Acc. Chem. Res. 2017, 50, 805-813.) MOFs have been utilized for drug delivery and enzyme fixation. (See, for example, Teplensky, M. H., et al., J. Am. Chem. Soc. 2017; Horcajada, P., et al., Nat. Mater. 2010, 9, 172-178; Zheng, H., et al., J. Am. Chem. Soc. 2016, 138, 962-9681; Dong, Z., et al., J. Am. Chem. Soc. 2017, 139, 14209-14216; Della Rocca, J., et al., Acc. Chem. Res 2011, 44, 957-968; Li, P., et al., Chem 2016, 1, 154-169; Wu, X., et al., Catal. Sci. Technol. 2015, 5, 5077-5085; Shieh, F.-K., et al., J. Am. Chem. Soc. 2015, 137, 4276-4279; and Deng, H., et al., Science 2012, 336, 1018-1023.) Though immobilization of biomolecules in MOFs could be realized through either de novo or post-synthetic methods, the use of MOF candidates as insulin oral delivery agents has not been realized due to the extremely acidic environment in the stomach (pH=1.5-3.5). (See, for example, Majewski, M. B., et al., Cryst Eng Comm 2017; Lyu, F., et al., Nano letters 2014, 14, 5761-5765; Liang, K., et al., Nat. Commun. 2015, 6; Chen, Y., et al., Inorg. Chem. 2012, 51, 9156-9158; and Lykourinou, V., et al., J. Am. Chem. Soc. 2011, 133, 10382-10385.)

SUMMARY

Mesoporous zirconium metal-organic frameworks (MOFs) having insulin immobilized therein and methods of using the MOFs in insulin delivery are provided.

The insulin-loaded metal-organic framework molecules include a porous zirconium metal-organic framework molecule and insulin molecules within pores of the porous zirconium metal-organic framework. The insulin-loaded metal-organic framework molecules can be delivered via oral administration to a patient.

Some embodiments of the insulin-loaded MOFs include a porous, channel-type zirconium metal-organic framework molecule having a csq-net topology and comprising eight $Zr_6$ nodes that are connected by organic linkers; and insulin molecules within pores of the zirconium metal-organic framework, wherein the diameters of the largest pores of the porous zirconium metal-organic framework molecule are the same as, or smaller than, the largest diameter of a pepsin enzyme.

Examples of porous, channel-type zirconium metal-organic framework molecule having a csq-net topology and comprising eight $Zr_6$ nodes that are connected by organic linkers include the MOFs designated NU-1000, NU-1003, NU-1004, NU-1005, NU-1006, PCN-128, PCN-222, and UMCM-313.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

A. 1A is a schematic representation of encapsulation of insulin in the mesopores of NU-1000 and exclusion of pepsin from the MOF framework.

solution. Insulin@NU-1000 withstands exposure to gastric acid and stomach acid and releases encapsulated insulin in PBS.

Figure 2B:
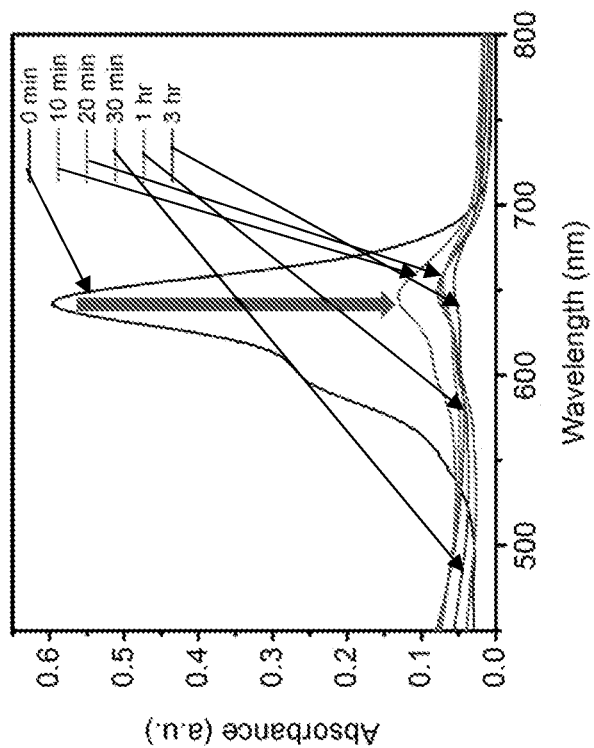
Figure 2A:
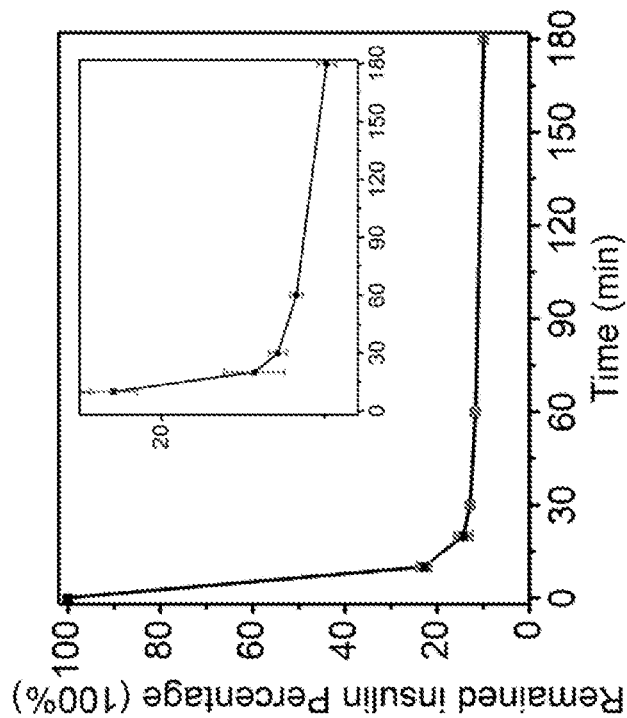

FIG. 2A shows the UV-vis spectra used to monitor a labeled insulin concentration in a supernatant at various time points after adding NU-1000. FIG. 2B shows the adsorption of AlexaFluor-647 labeled insulin in NU-1000 crystals.

Figures 3A, 3B:
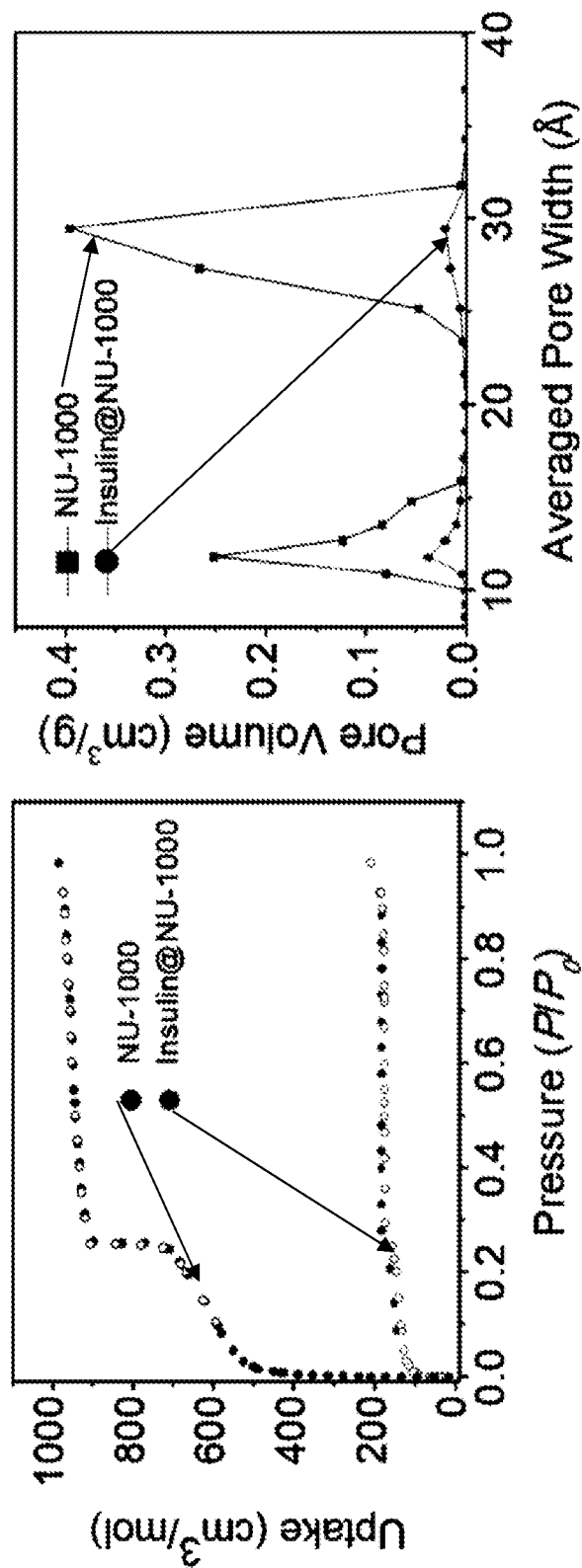
Figures 3C, 3D:
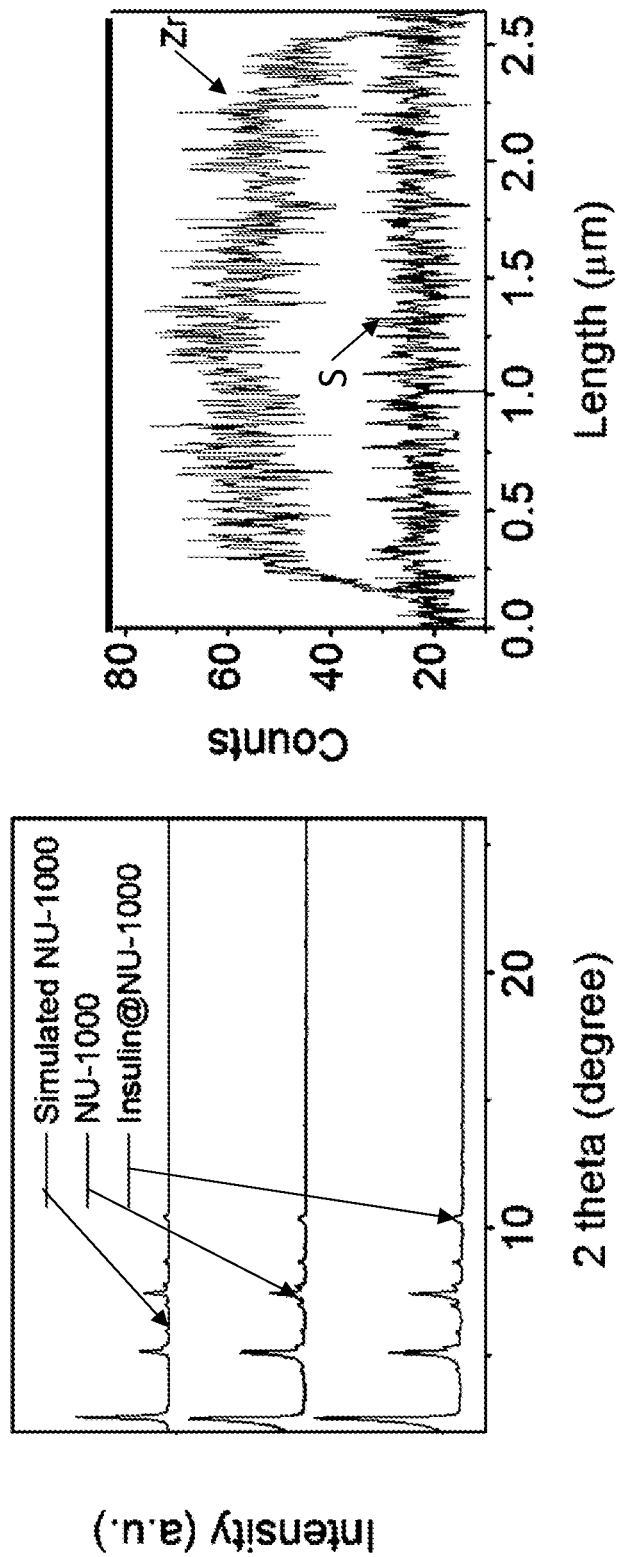

FIG. 3A shows that $N_2$ adsorption-desorption isotherms reveal significant surface area reduction after encapsulation of insulin. FIG. 3B shows Density Functional Theory (DFT) pore size distributions of NU-1000 (black) and insulin@NU-1000 (grey), indicating insulin occupies both the mesopores and micropores. FIG. 3C depicts Powder X-ray Diffraction (PXRD) patterns of NU-1000, simulated NU-1000, and insulin@NU-1000, confirming the retention of crystallinity. FIG. 3D is an Energy Dispersive X-ray Spectroscopy (EDX) line scan for Zr and S, which confirms uniform distribution of insulin throughout crystal in insulin@NU-1000.

Figure 4A:
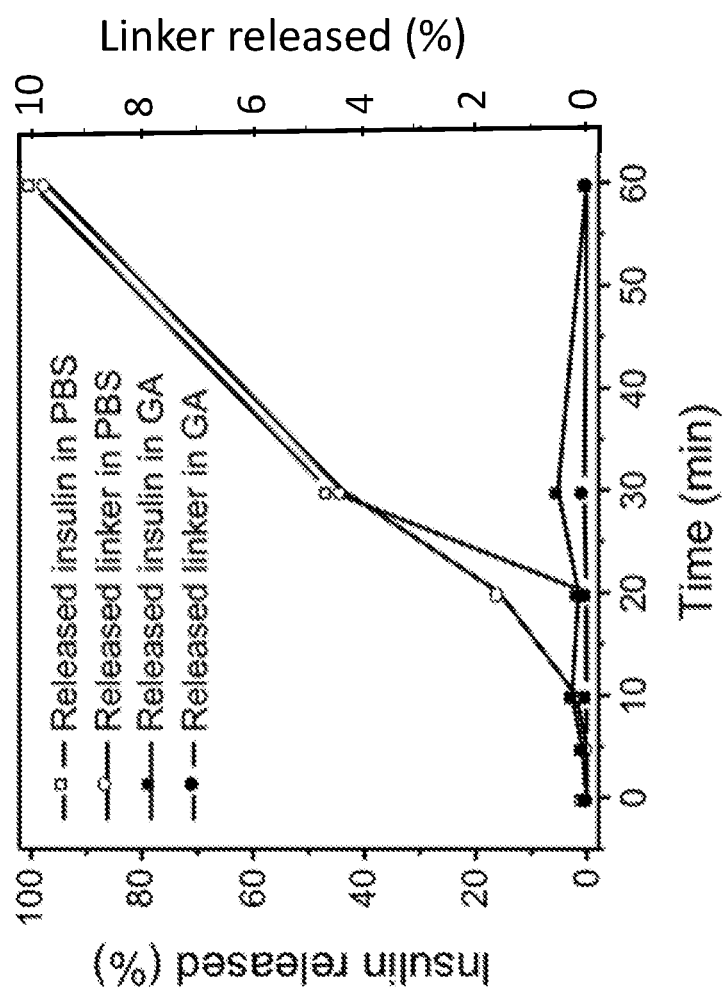
Figure 4B:
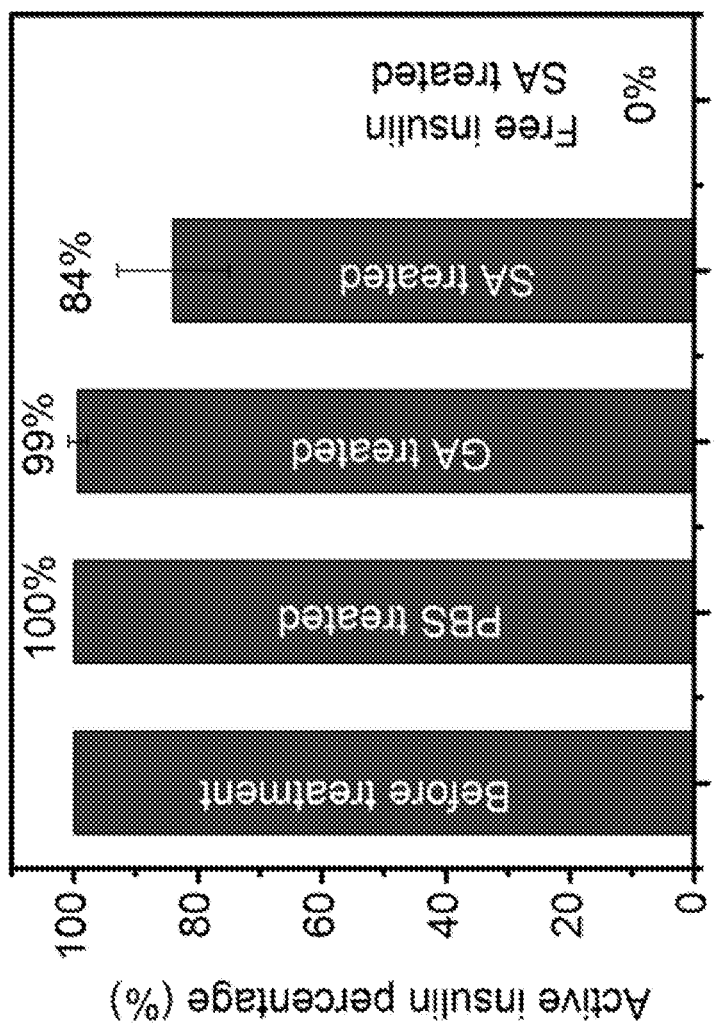

FIG. 4A shows the percent of encapsulated insulin released from insulin@NU-1000 and the degradation of NU-1000 crystals vs. time under different conditions. FIG. 4B shows the concentration of active insulin after loading and treatment under various harsh conditions. The first column shows the original concentration of active insulin in solution. The other columns show the amount of active insulin released from insulin@NU-1000 after different treatments (GA for gastric acid and SA for stomach acid).

Figure 5A:
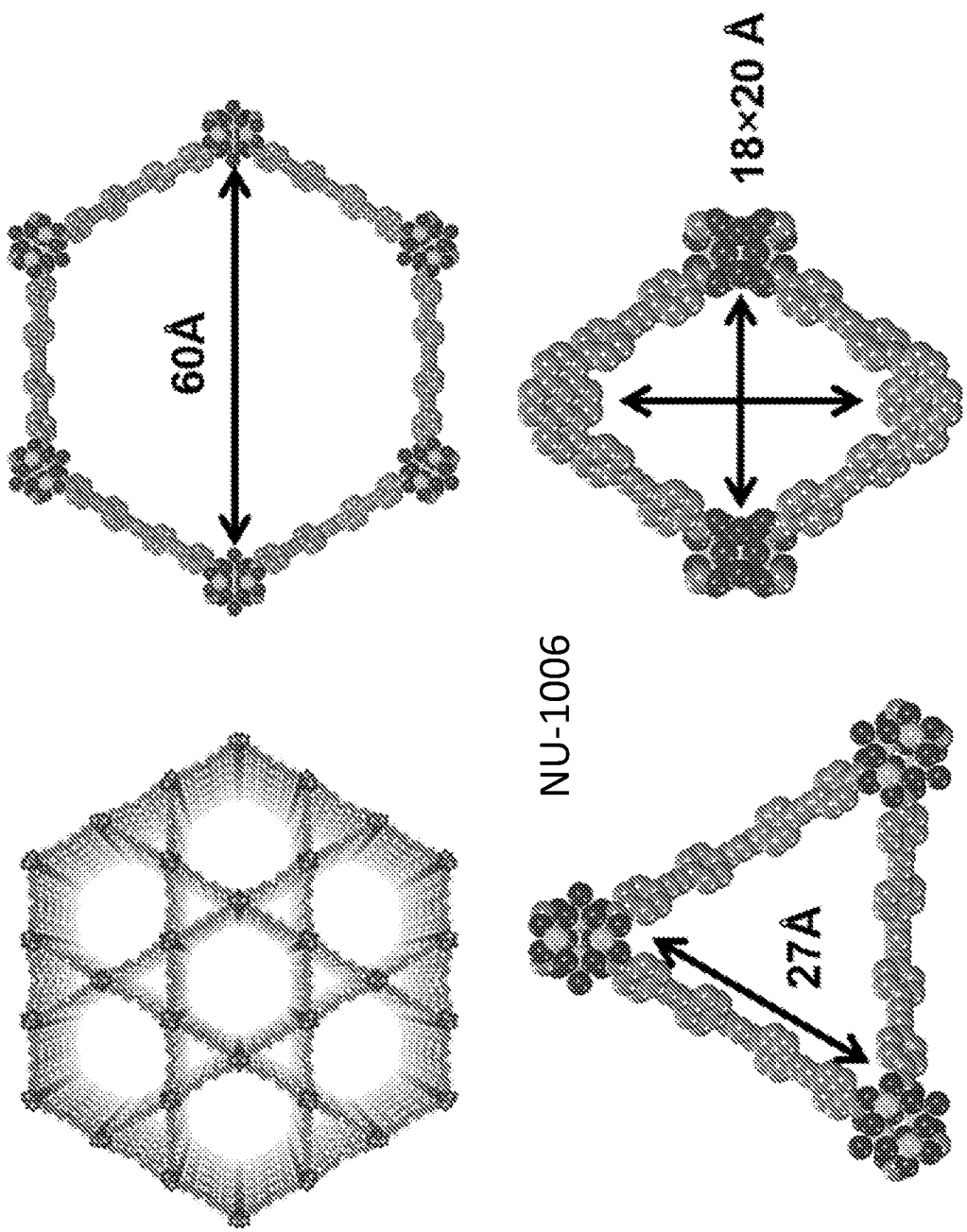
Figure 5B:
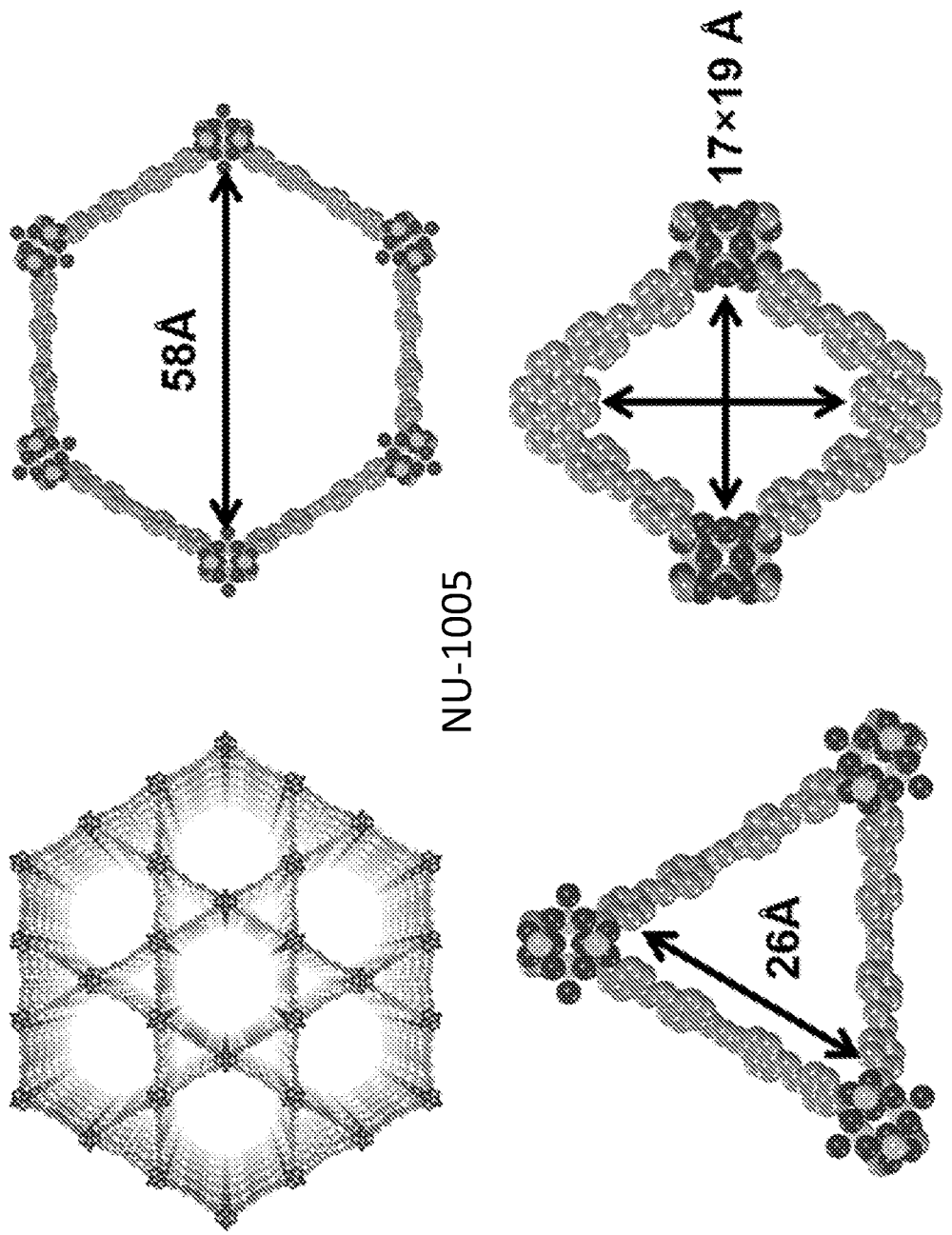
Figure 5C:
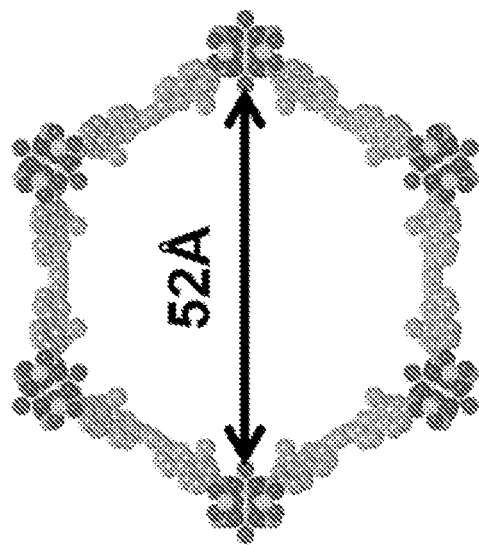
Figure 5C:
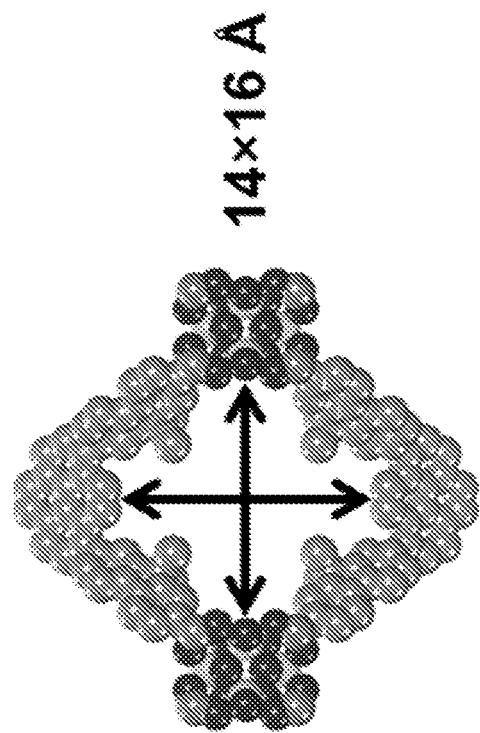
Figure 5C:
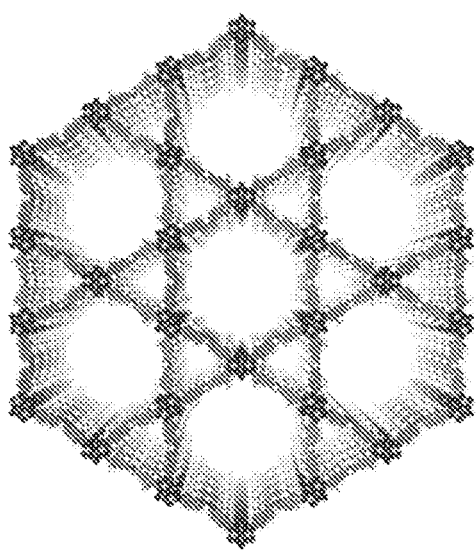
Figure 5C:
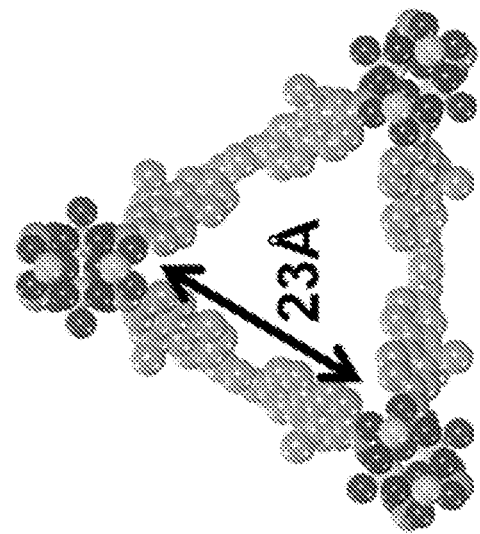
Figure 5D:
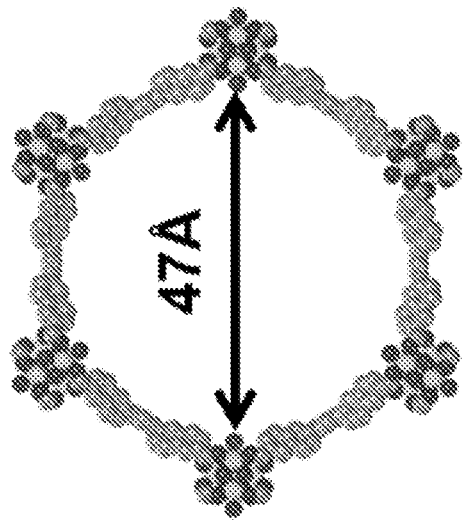
Figure 5D:
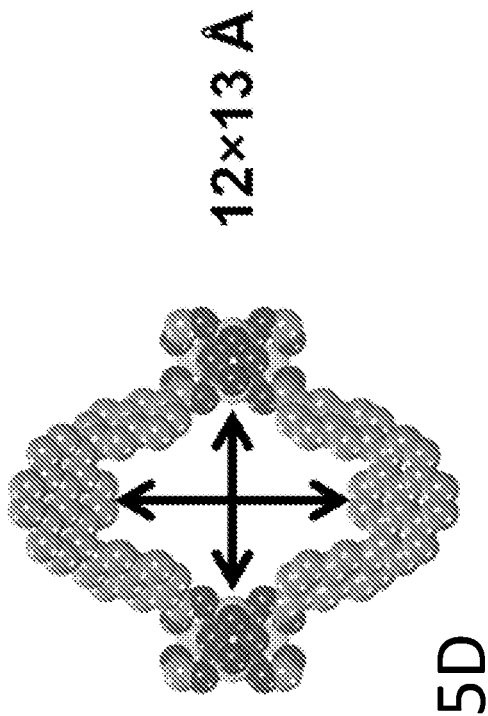
Figure 5D:
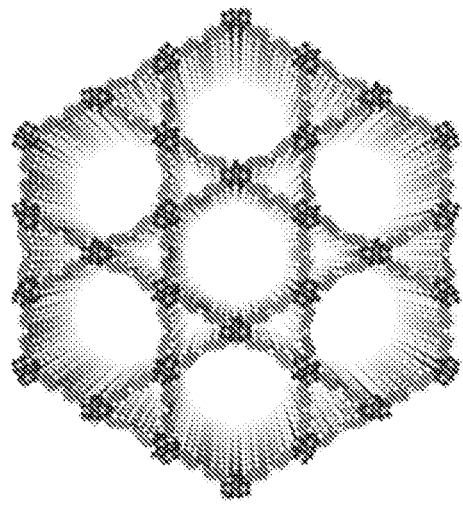
Figure 5D:
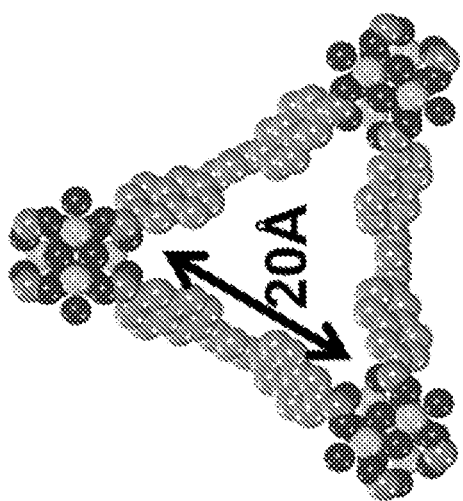
Figure 5E:
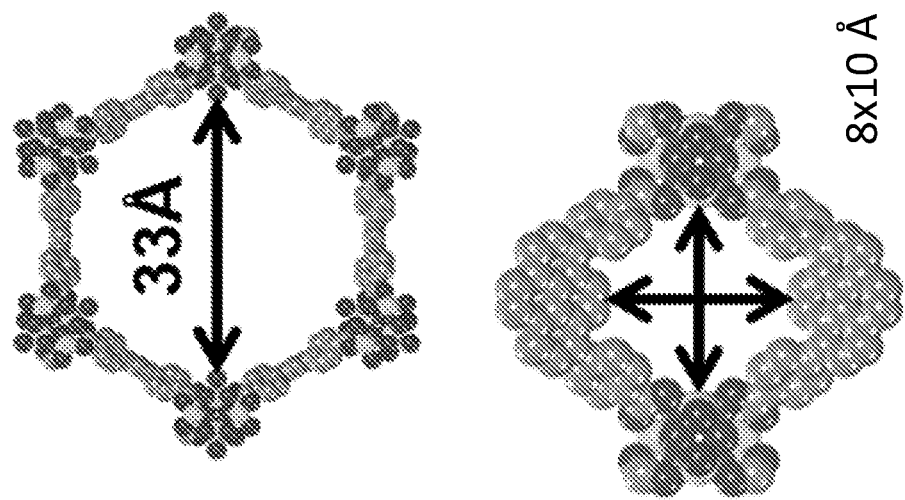
Figure 5E:
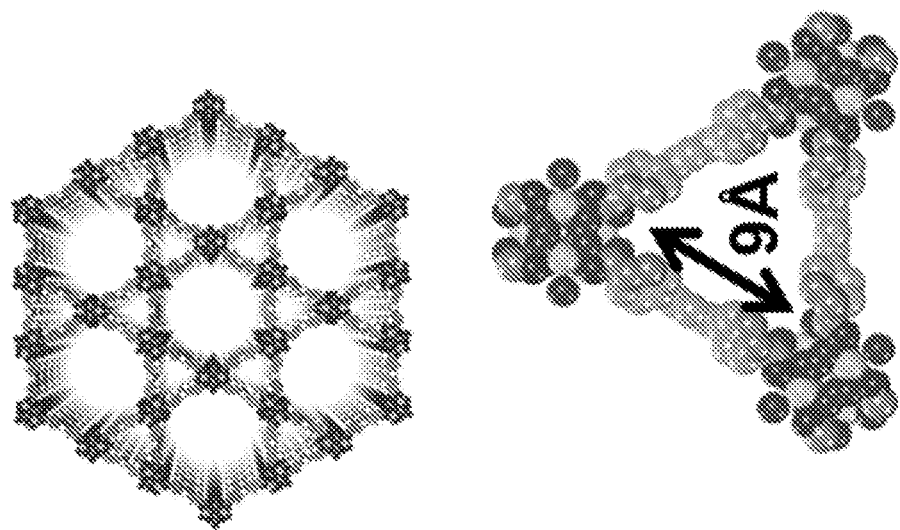

FIG. 5A shows the structure of MOF NU-1006. FIG. 5B shows the structure of MOF NU-1005. FIG. 5C shows the structure of MOF NU-1004. FIG. 5D shows the structure of MOF NU-1003. FIG. 5E shows the structure of MOF NU-1000.

Figure 6:
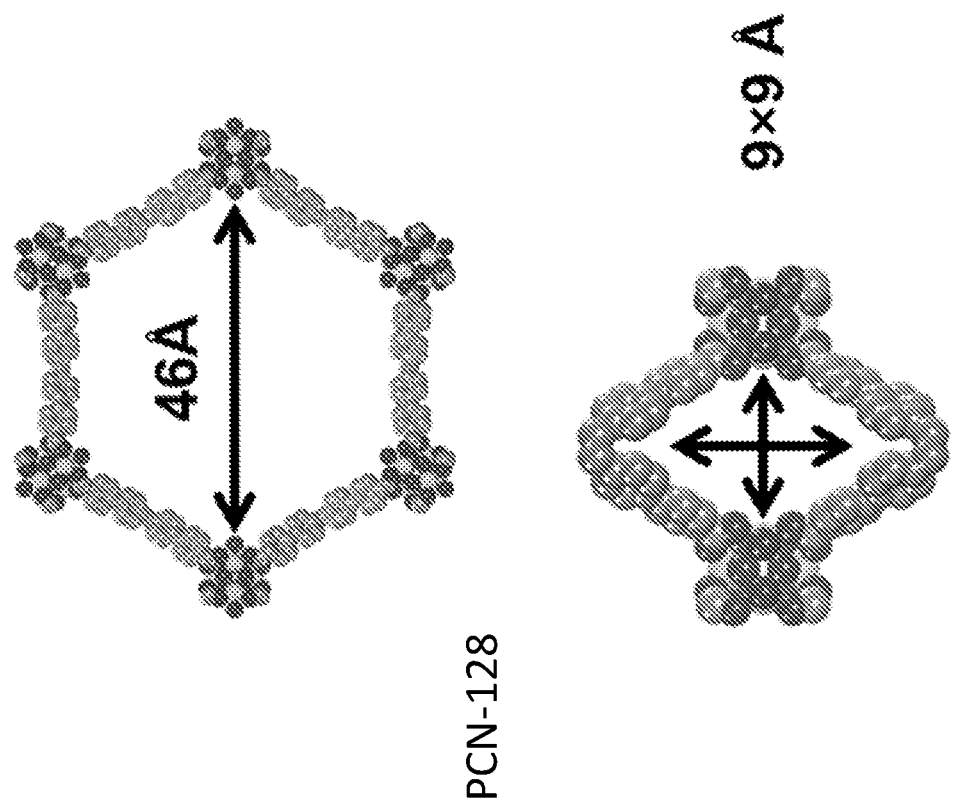
Figure 6:
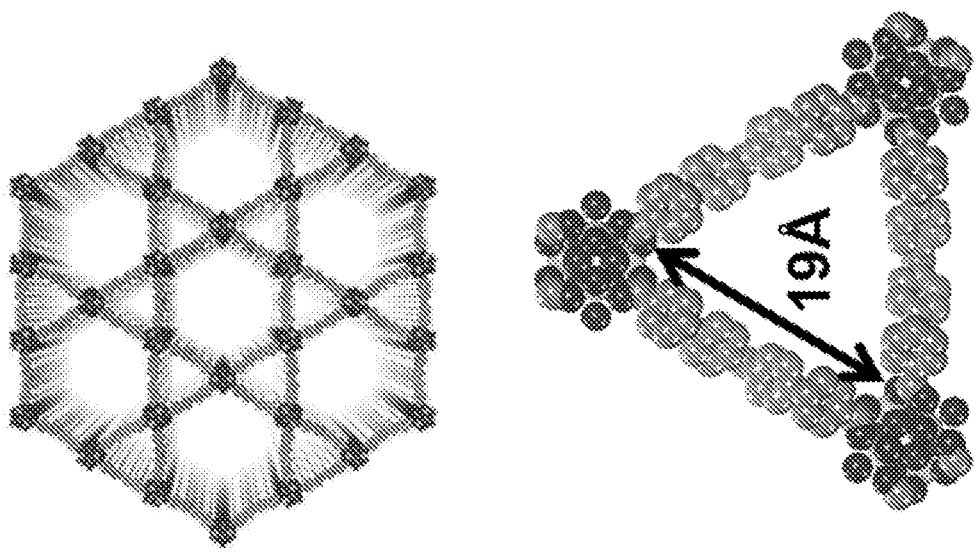

FIG. 6 shows the structure of MOF PCN-128.

Figure 7:
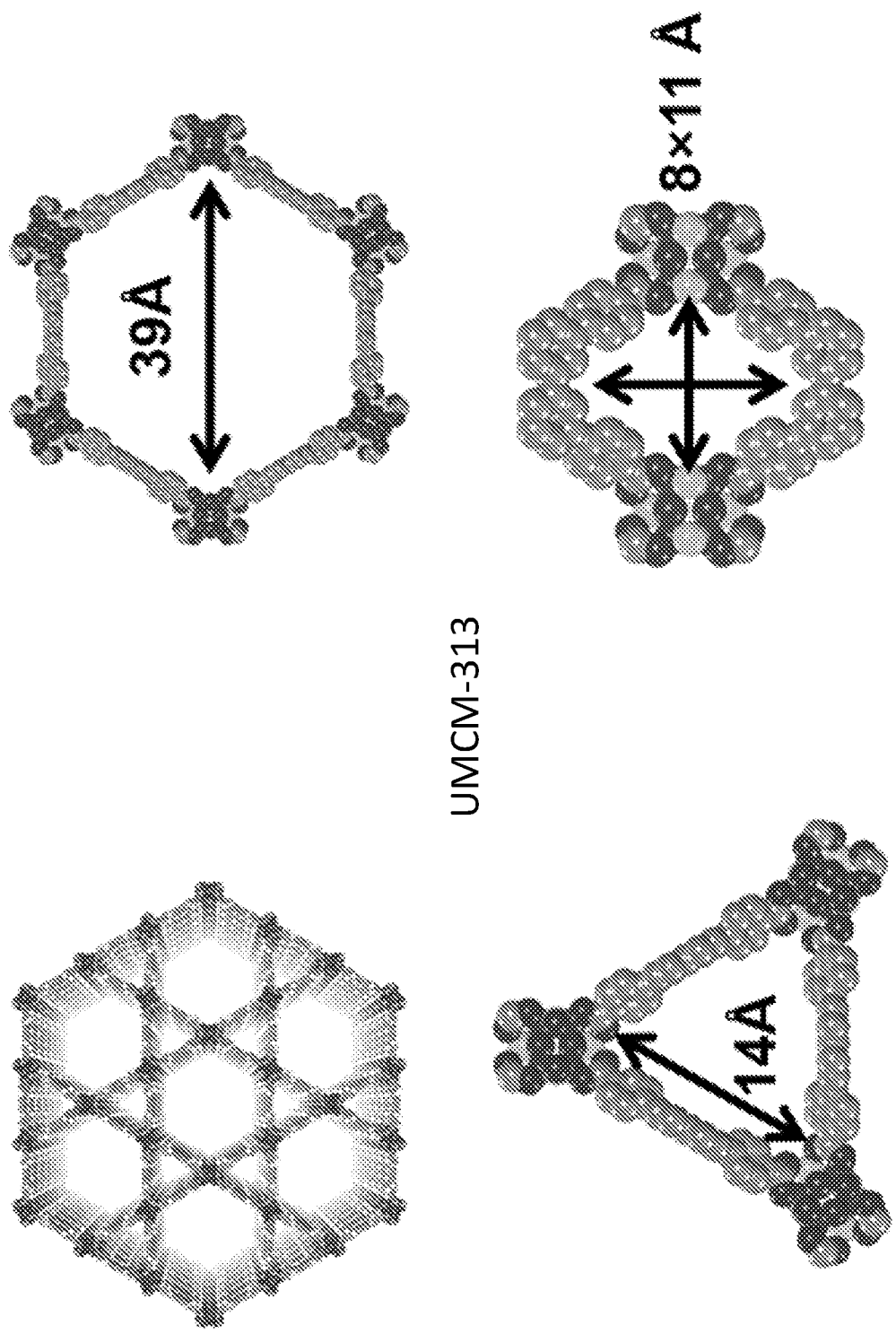

FIG. 7 shows the structure of MOF UMCM-313.

Figure 8:
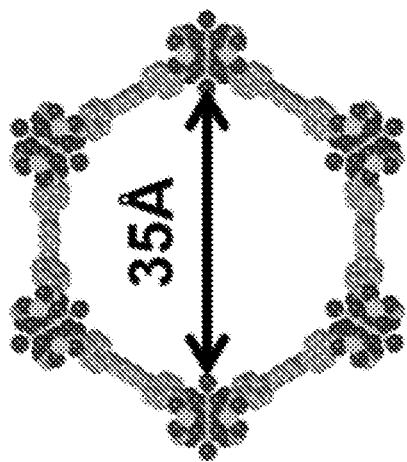
Figure 8:
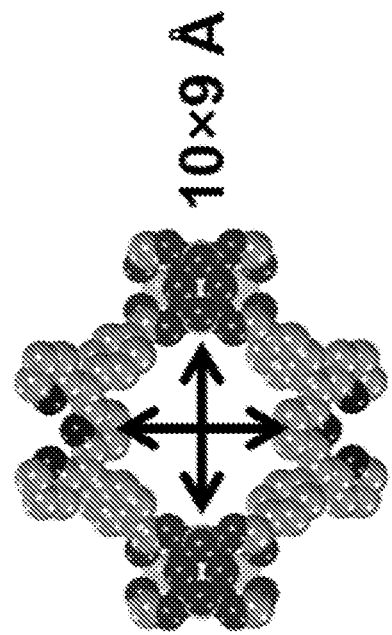
Figure 8:
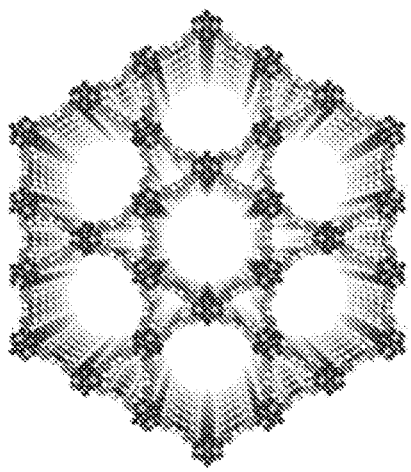
Figure 8:
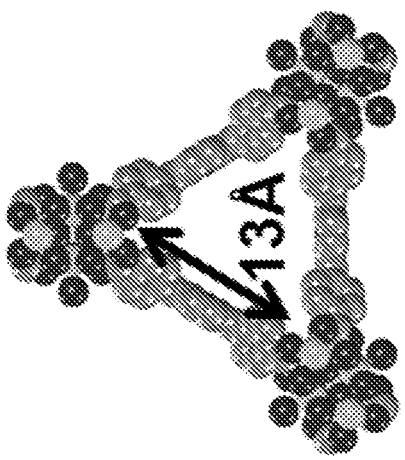

FIG. 8 shows the structure of MOF PCN-222.

Figure 9:
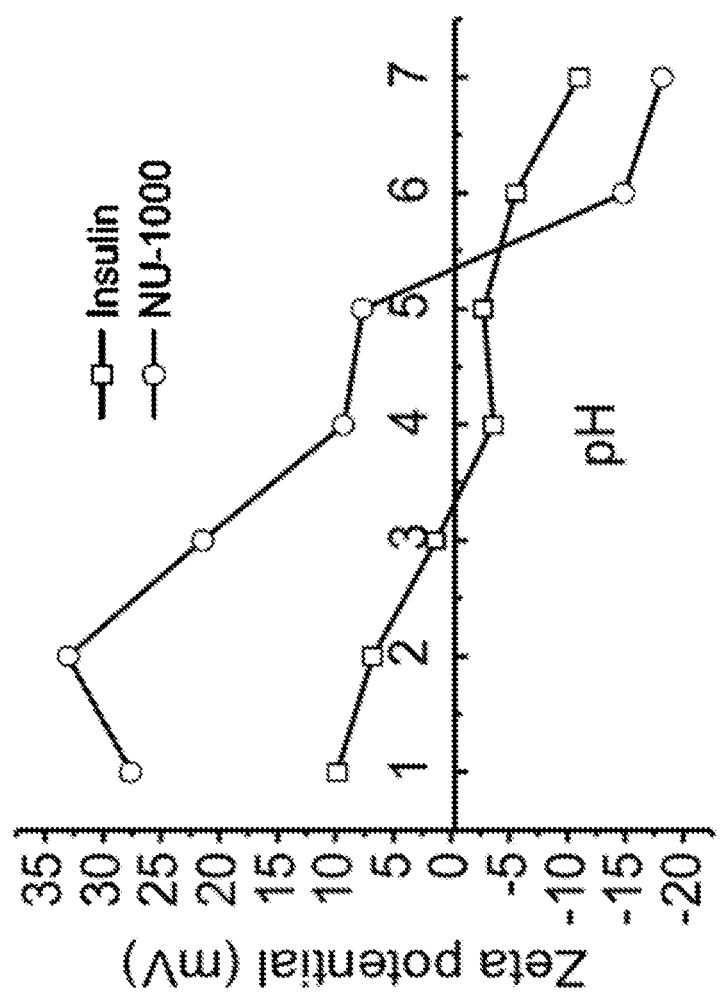

FIG. 9 depicts the Zeta potential of insulin and NU-1000 crystals in different conditions.

Figure 10:
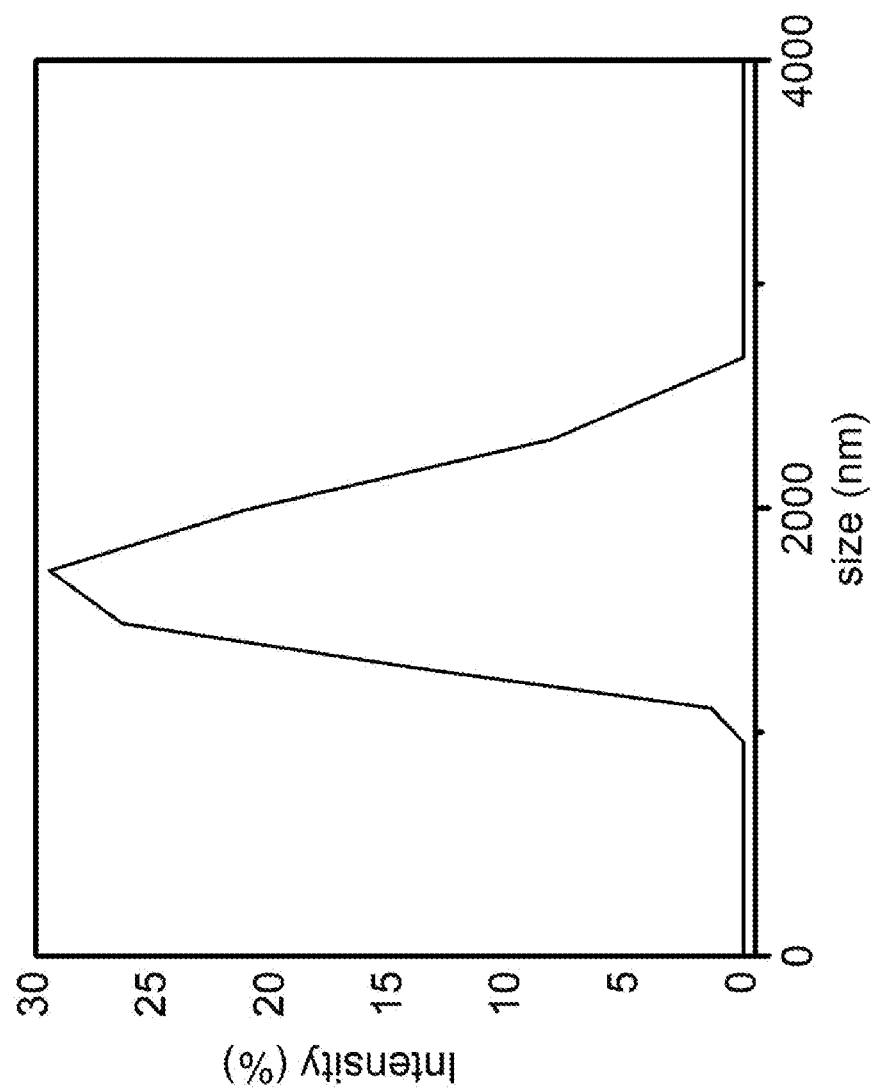

FIG. 10 shows the size distribution of NU-1000 crystals.

Figure 11:
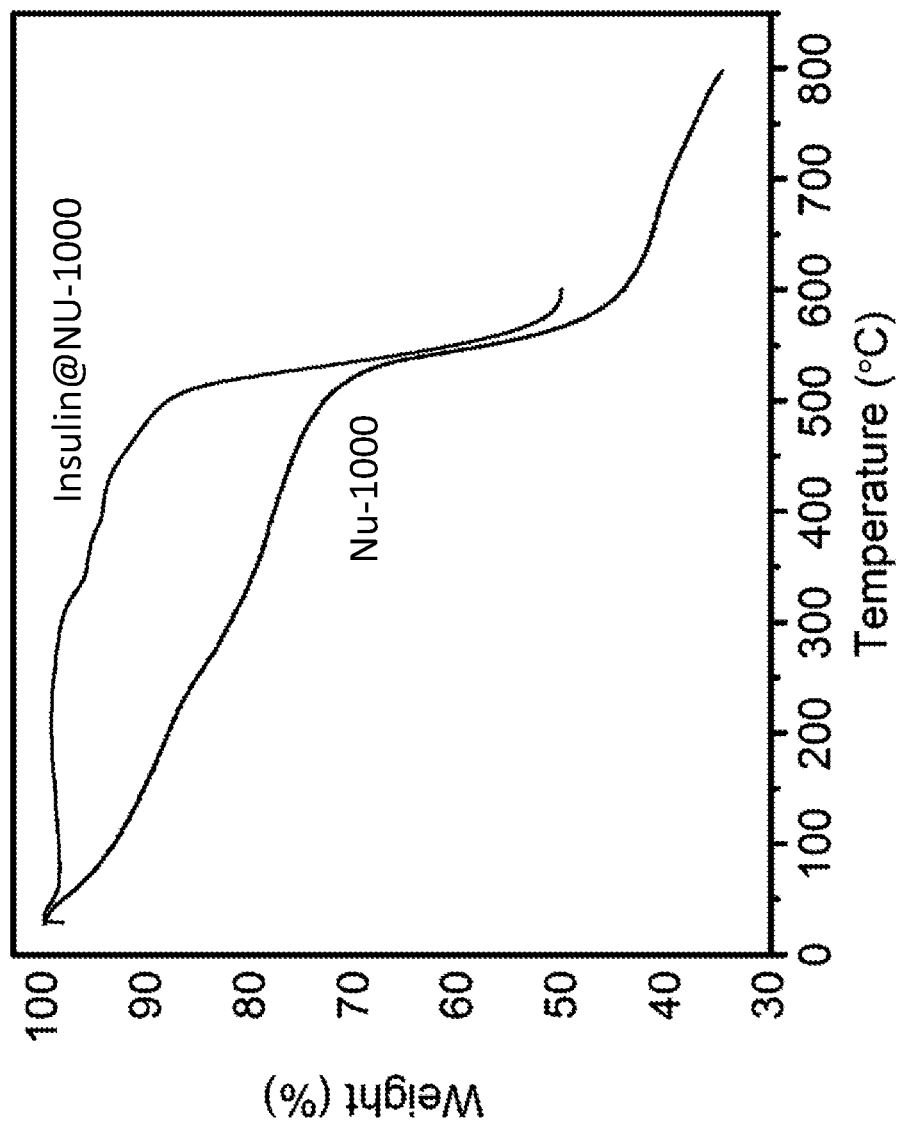

FIG. 11 depicts a thermogravimetric analysis of NU-1000 crystals and insulin@NU-1000.

Figure 12:
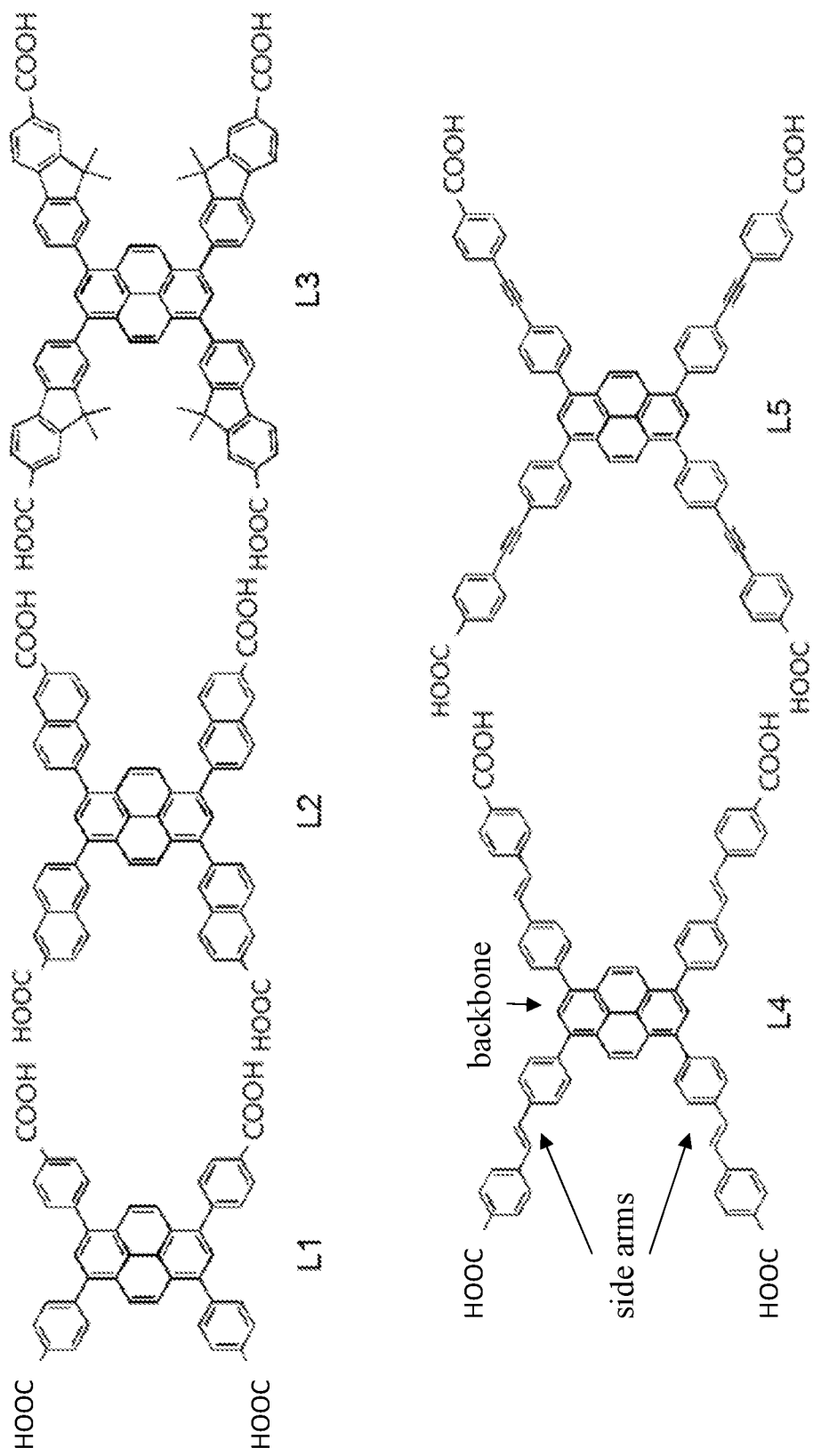

FIG. 12 shows organic linkers that can be used to construct MOFs NU-1000, NU-1003, NU-1004, NU-1005, and NU-1006.

Figure 13A:
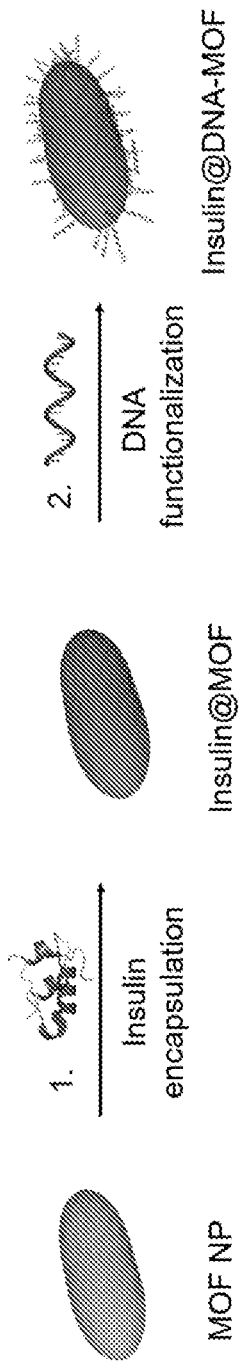
Figure 13B:
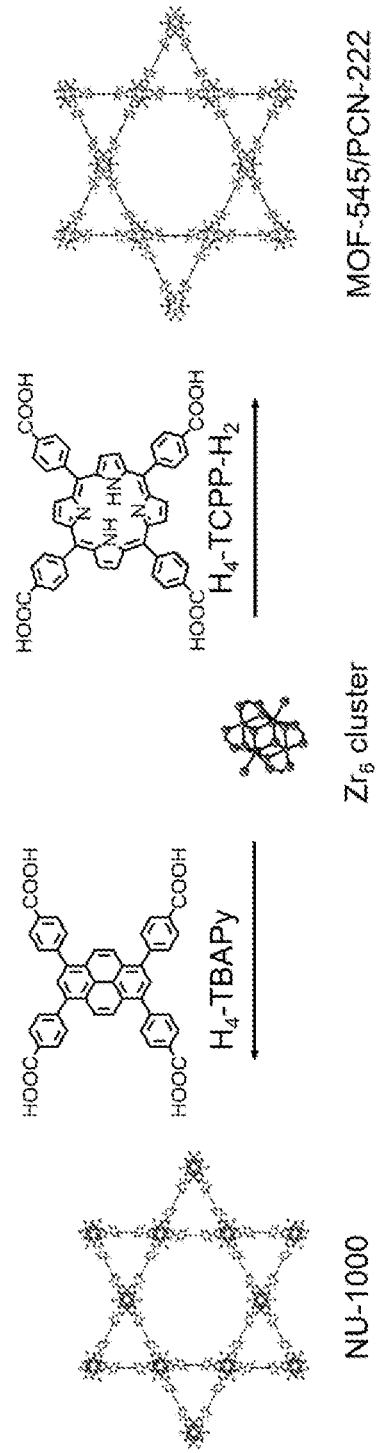
Figure 13C:
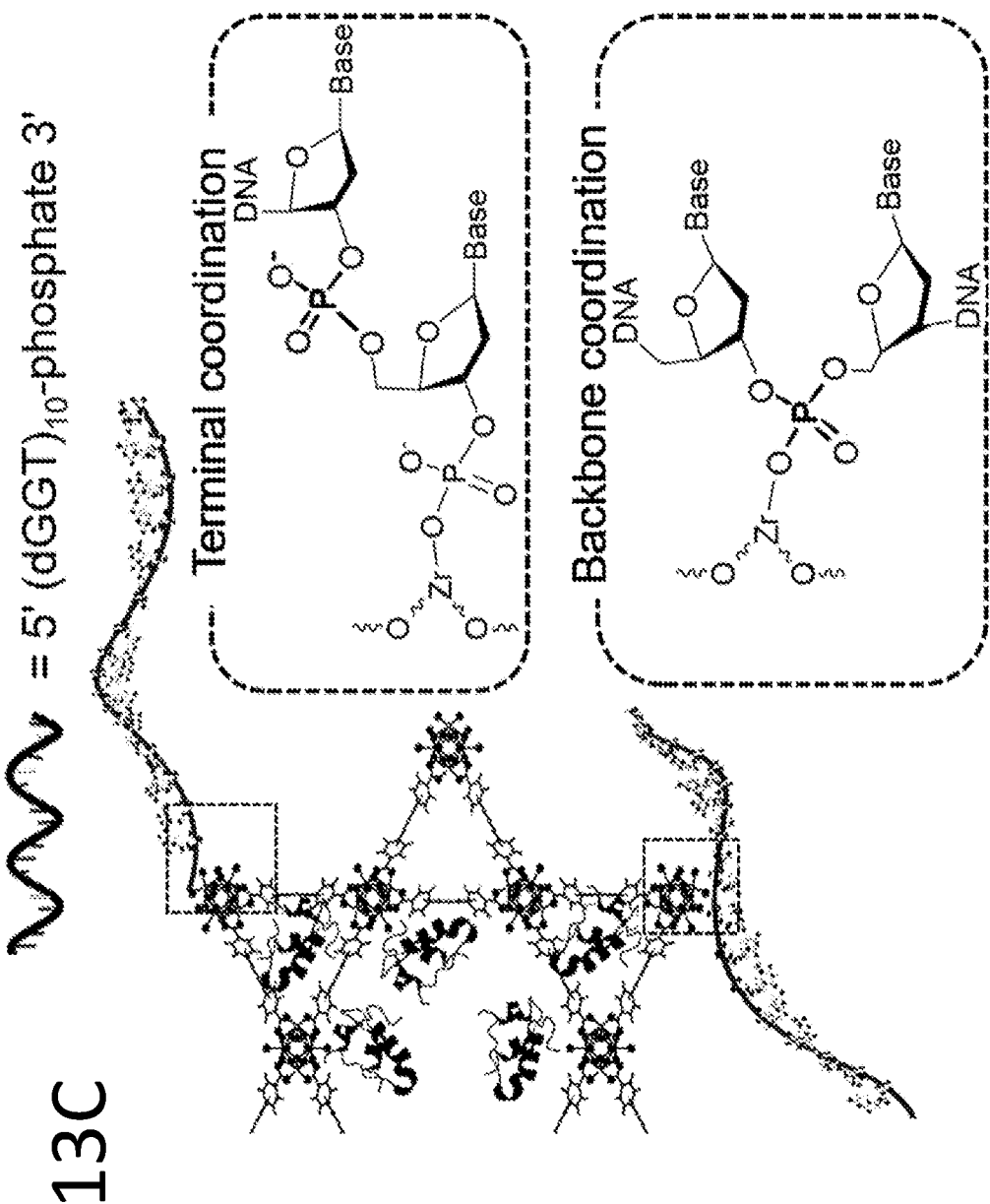

FIG. 13A shows a schematic illustration of insulin encapsulation in the mesoporous channels of MOF NPs followed by DNA surface functionalization. FIG. 13B shows crystal structures of two mesoporous Zr MOFs: NU-1000 and PCN-222/MOF-545 and their respective organic linkers. FIG. 13C shows DNA functionalization of insulin encapsulated MOF NPs using 3' terminal phosphate modified nucleic acids. FIG. 13C discloses SEQ ID NO: 1.

Figure 14A:
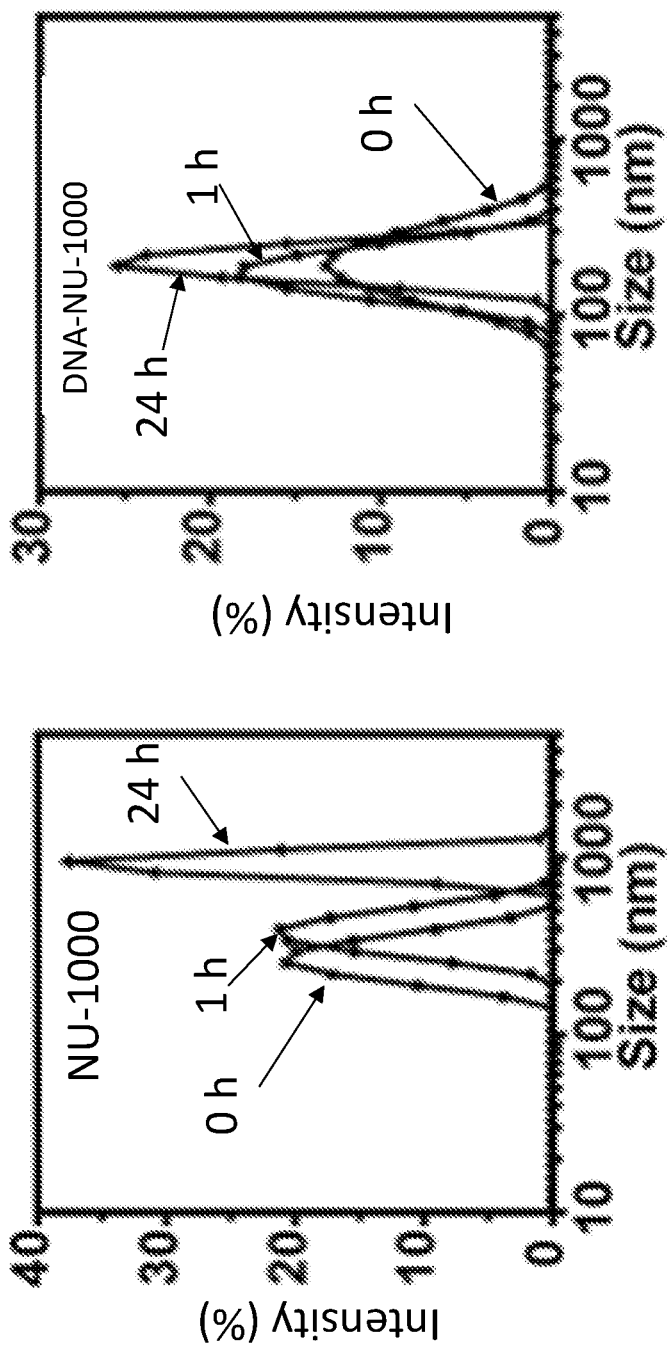
Figure 14B:
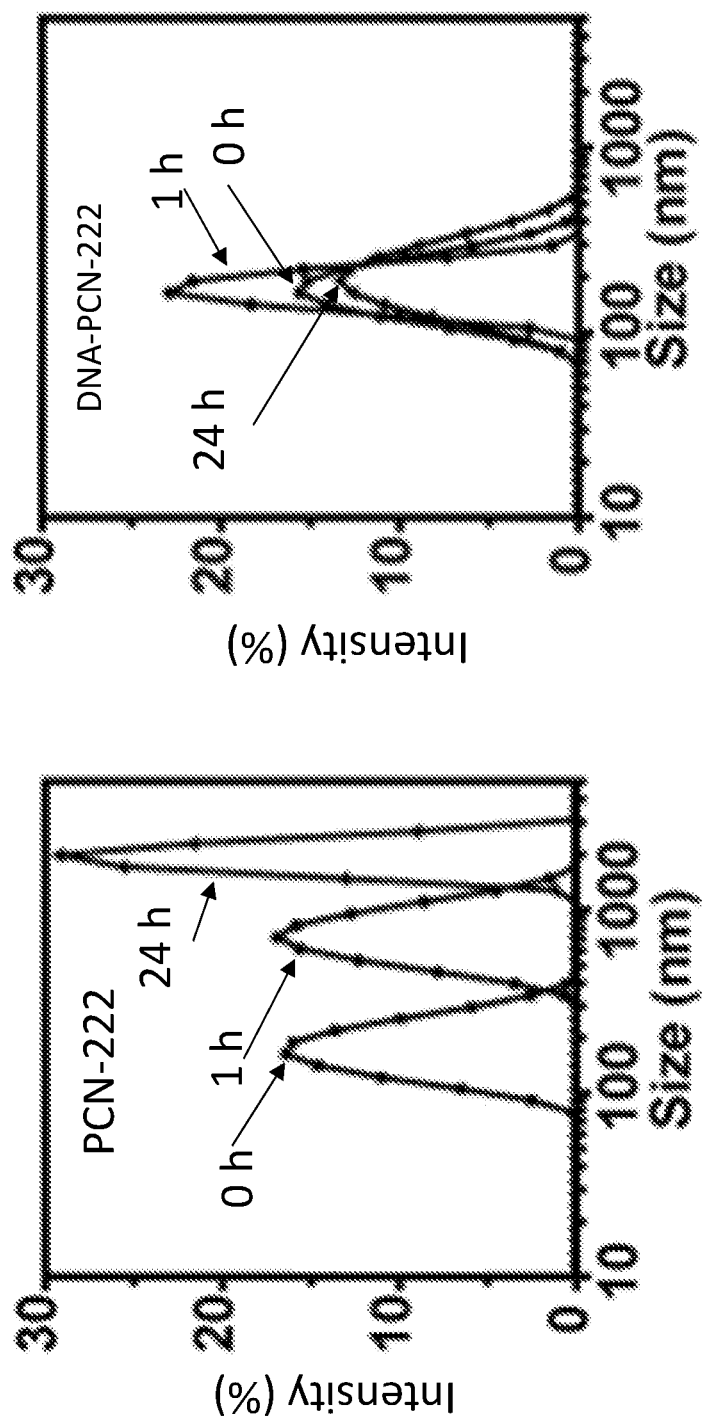

FIG. 14A and FIG. 14B show colloidal stability of NU-1000 and PCN-222 NPs in cell medium, as determined by DLS without (left) and with DNA surface modification (right). Scale bars=100 nm.

Figure 15:
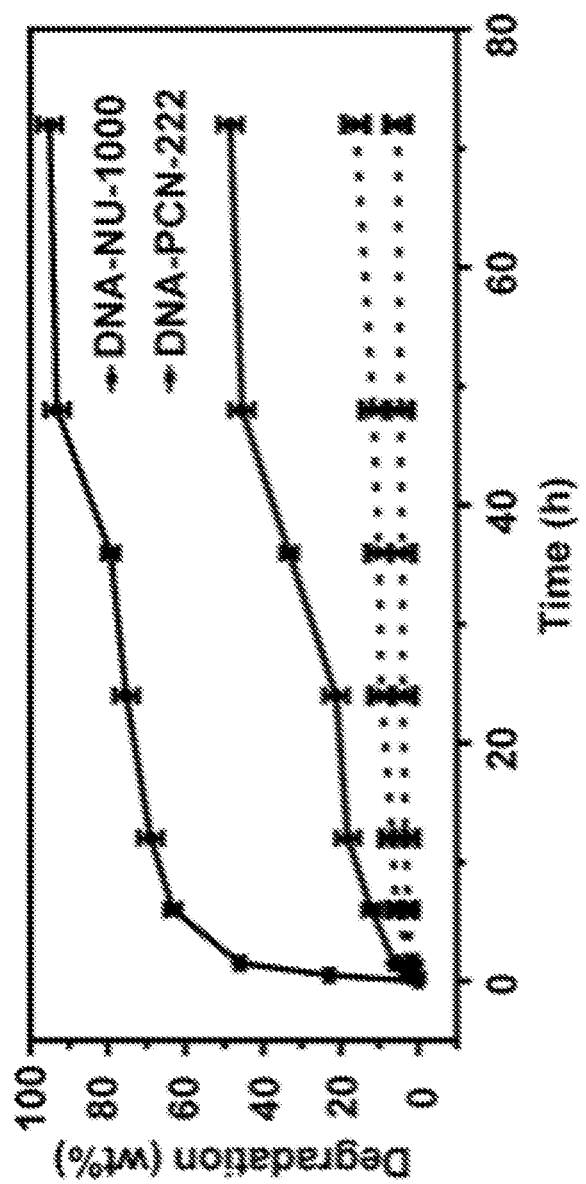

FIG. 15 shows degradation profiles of DNA-NU-1000 NPs and DNA-PCN-222 NPs incubated in extracellular medium (dashed lines) and in simulated intracellular medium (solid lines) at 37° C. with 400 rpm shaking.

Figure 16A:
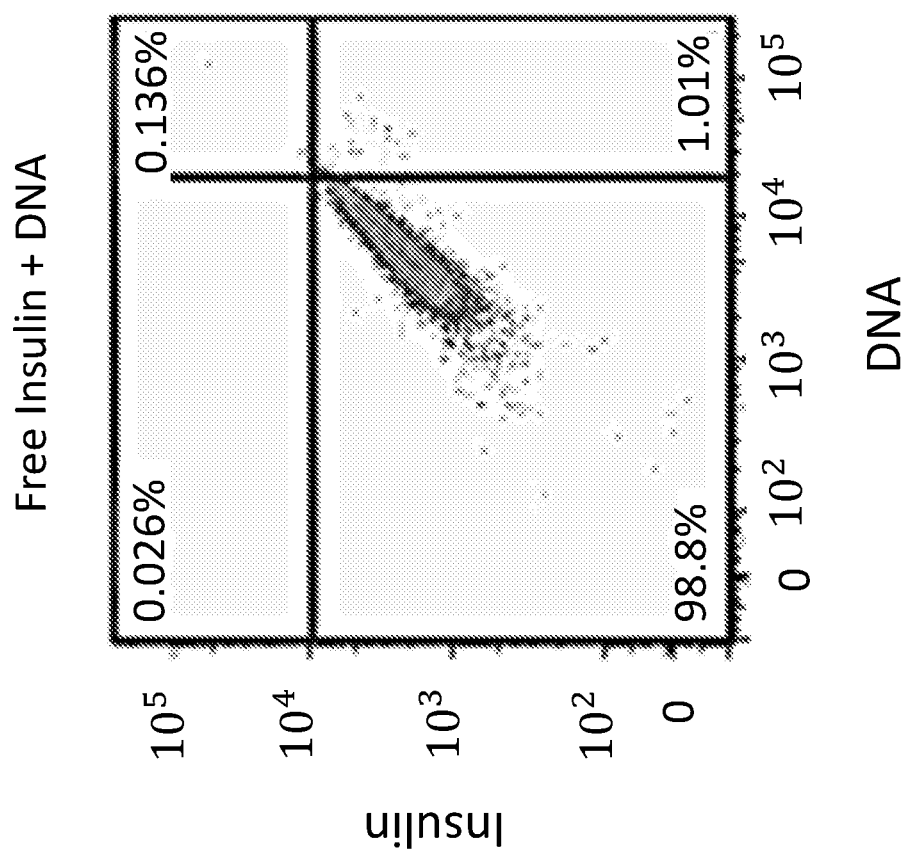
Figure 16B:
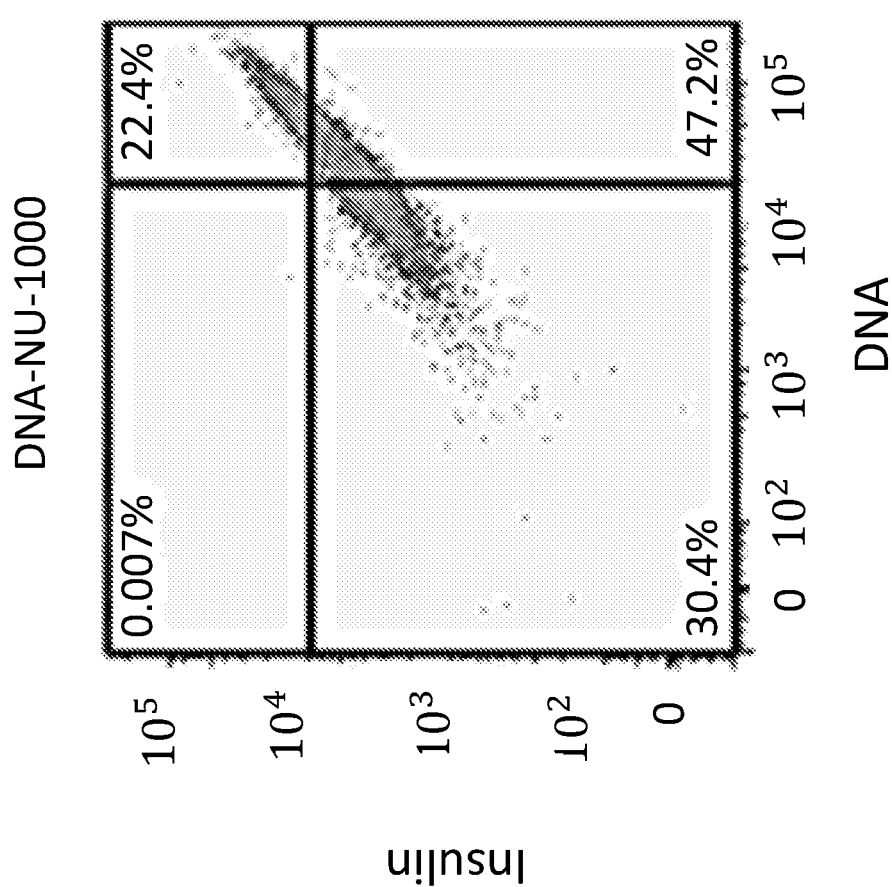
Figure 16C:
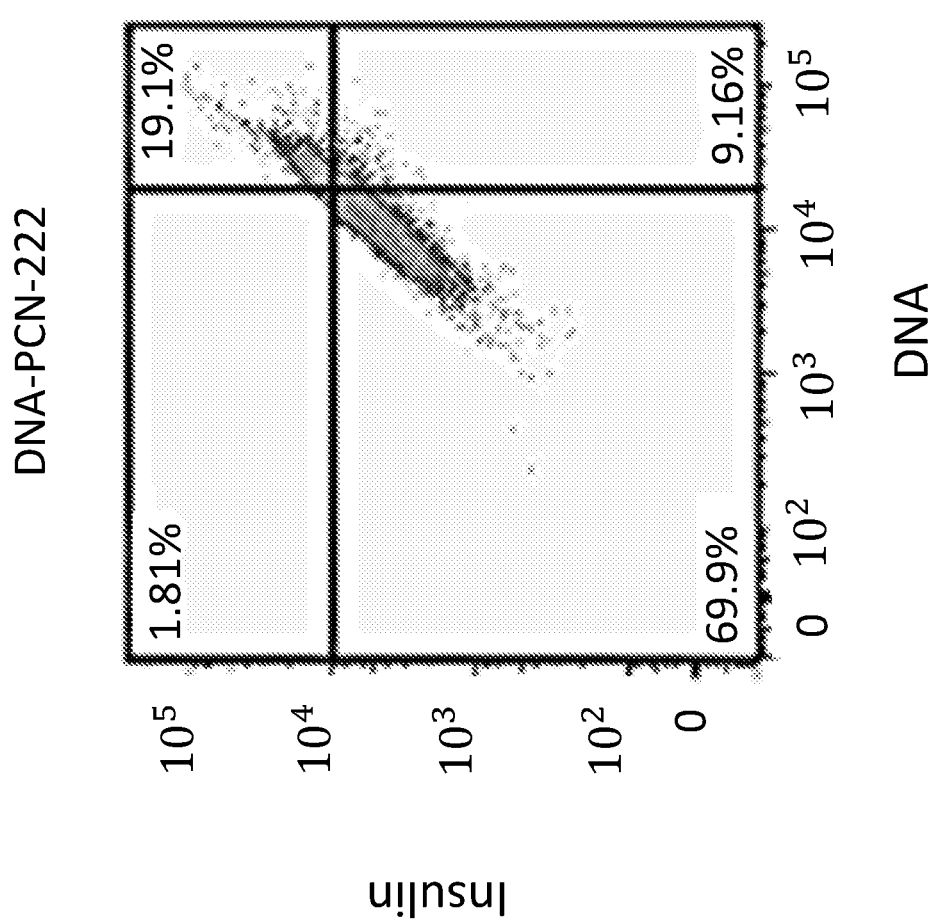
Figure 16D:
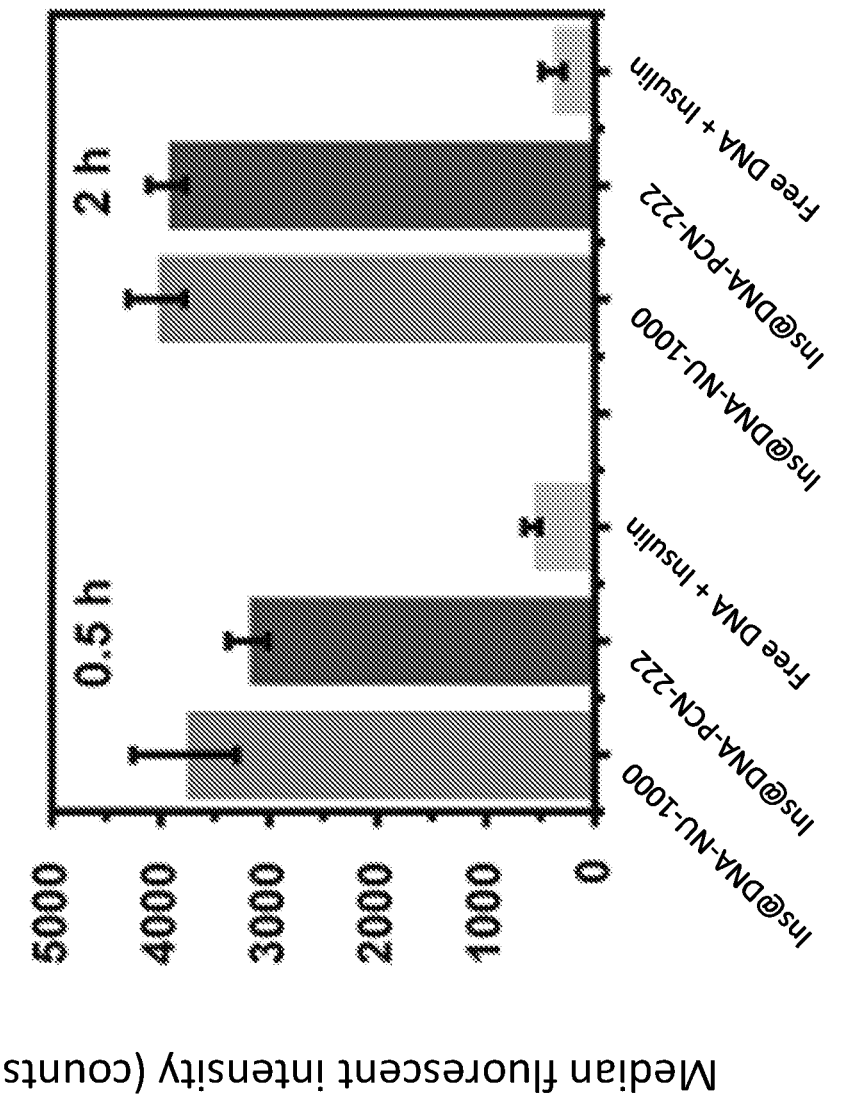
Figure 16E:
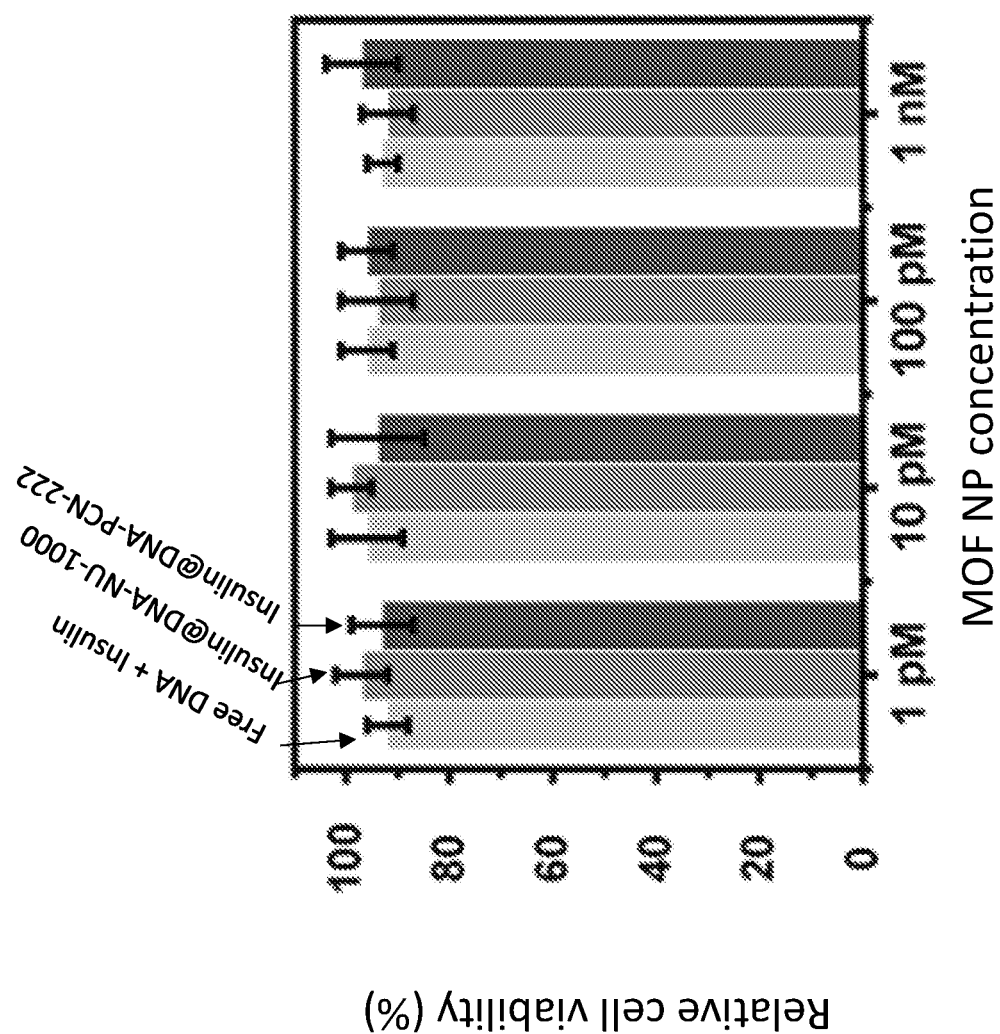

FIG. 16A-FIG. 16C show flow cytometry plots of SK-OV cells after 6 h treatment with free insulin+DNA (FIG. 16A), insulin@DNA-NU-1000 (FIG. 16B), and insulin@DNA-PCN-222 (FIG. 16C). FIG. 16D shows cellular uptake of insulin delivered in different constructs as determined by flow cytometry. Fluorescence at 647 nm was measured in SK-OV cells after treatment with insulin at various incubation time (0.5 h and 2 h). FIG. 16E shows that MTT assay verifies no appreciable cytotoxicity induced by insulin@DNA-PCN-222 and insulin@DNA-NU-1000 NPs. Scale bar=10 μm.

DETAILED DESCRIPTION

Mesoporous MOFs having insulin immobilized therein and methods of using the MOFs in insulin delivery are provided. The MOFs include zirconium MOFs having a csq-net topology. The insulin-loaded MOFs are acid-stable and can prevent insulin from denaturing and degrading in the presence of stomach acid and/or in the presence of the digestive enzyme, pepsin. Moreover, the encapsulated insulin can be released from the MOFs under physiological conditions without significant loss of activity when compared to free insulin.

MOFs are hybrid, crystalline, porous materials made from metal-ligand networks that include inorganic nodes connected by organic linkers. The inorganic nodes (also referred to as vertices) in the framework are composed of metal ions or clusters. By convention, carboxylates (or other linker terminal groups or atoms) are often represented as components of the nodes. These nodes are connected by coordination bonds to organic linkers, which commonly contain carboxylate, phosphonate, pyridyl, and imidazolate or other azolate functional groups.

Immobilization of insulin in zirconium MOFs is beneficial because: (1) various embodiments of zirconium MOFs can survive in neutral to acidic solution (pH as low as 1; for example a pH range from 1 to 3); (2) the pore sizes and surfaces of various zirconium MOFs can be tailored to interact favorably with insulin and increase insulin loading; and (3) phosphate ions in the blood stream can irreversibly cleave the node-linker bonds in zirconium MOF carriers and release the insulin naturally.

The zirconium MOFs include channel-type MOFs that present an interconnected hierarchical pore structure comprising a first set of large hexagonal channels and a second set of smaller triangular channels running alongside of the large hexagonal channels. The channels are large enough to allow for insulin infiltration and immobilization but small enough to prevent pepsin from infiltrating the MOF and digesting the insulin. Thus, at least some channels in the MOFs have diameters (pores) that are larger than the largest dimensions of insulin. The widest channels desirably have diameters (pores) that are the approximately the same as, or smaller than, the largest dimension of pepsin (approximately 62 Å) and, more desirably, smaller than the smallest dimension of pepsin. By way of illustration, the largest pore diameter in the MOFs may be 62 Å or smaller. This includes MOFs in which the largest pore diameter is 60 Å or smaller, further includes MOFs in which the largest pore diameter is 50 Å or smaller, further includes MOFs in which the largest pore diameter is 40 Å or smaller, and still further includes MOFs in which the largest pore diameter is 30 Å or smaller. The largest pores in some embodiments of the MOFs have diameters in the range from 30 Å to 45 Å.

MOFs having a csq-net topology include mesoporous zirconium MOFs having eight $Zr_6$ cluster nodes connected by tetratopic linkers, where a $Zr_6$ cluster node has the structure $Zr_6(\mu_3\text{-O})_4(\mu_3\text{-OH})_4(OH)_4(H_2O)_4$ or a variation of that structure in which some or all of the hydroxo ligands are replaced with oxo and/or hydroxo ligands. The tetratopic linkers have a backbone and side arms. The linkers can include various aryl groups in their linker backbones and side arms, including phenyl groups, bi-phenyl groups, and napthyl groups. For example, one family of such MOFs has pyrene-based tetratopic linkers connecting the metal cluster nodes. Such linkers are designated "pyrene-based" because they include a pyrene group in their backbone. The structure of these types of MOFs is illustrated in FIGS. 5A, 5B, 5C, 5D, and 5E, which show MOFs designated NU-1006, NU-1005, NU-1004, NU-1003, and NU-1000, respectively. The MOF denoted NU-1000 is described in detail in Mondloch, et al., *J. Am. Chem. Soc.* 135, 10294-10297 (2013). NU-1000 has hexagonal channels with a diameter of 3.1 nm as well as triangular channels with an edge length of 1.5 nm, with windows connecting the two channels.

MOFs NU-1000, NU-1003, NU-1004, NU-1005, and NU-1006 are an isoreticular series of pyrene-based csq-net Zr-based MOFs with pore aperture diameters ranging from 3.3 to 6.2 nanometers. These MOFs differ in the side arm structures of their tetratopic linkers. NU-1000 has benzene groups in its side arms; NU-1003 has naphthalene groups in its side arms; NU-1004 has fluorene groups in its side arms; NU-1005 has stilbene groups in its side arms; and NU-1006 has diphenylacetate groups in its side arms. The chemical structures of organic linkers, L1-L5, that can be used to construct NU-1000, NU-1003, NU-1004, NU-1005, and NU-1006, respectively, are shown in FIG. 12.

Other csq-net topology MOFs include MOFs, such as PCN-128, which have eight $Zr_6$ cluster nodes connected by ethene-1,1,2,2-tetrayl)tetrakis-(([1,1'-biphenyl]-4-carboxylic acid))) (ETTC) linkers. The structure of the PCN-128 MOF is shown in FIG. 6 and described in Zhang et al., *J. Am. Chem. Soc.*, 2015, 137, 10064-10067, which is incorporated herein for the purposed of describing the structure of the MOF. Still other csq-net topology MOFs have $Zr_6$ cluster nodes connected by parylene-based tetratopic linkers. The structure for one such MOF, UMCM-313, is shown in FIG. 7 and described in Ma et al., *Cryst. Growth Des.*, 2016, 16 (7), pp 4148-4153, which is incorporated herein by reference for the purpose of describing the structure of the MOF. MOFs having a csq-net topology formed from $Zr_6$ clusters connected by porphyrin-based linkers can also be used. FIG. 8 shows the structure of one such MOF, denoted PCN-222. In each of FIGS. 5A-5E, 6, 7, and 8, the approximate diameter of the larger, hexagonal channel, the approximate side length of the smaller, triangular channel, and the approximate height and width dimensions of the windows between the large and small channels are provided. The diameters of the diagonal hexagonal pores of the csq-net zirconium MOFs described above are in the order: NU-1006 (62 Å)>NU-1005 (60 Å)>NU-1004 (51 Å)>NU-1003 (47 Å)>PCN-128 (46 Å)>UMCM-313 (39 Å)>PCN-222 (35 Å)>NU-1000 (33 Å). Methods for making these MOFs are illustrated in PCT application number WO/2017213871 and in Example 2.

The insulin loading in the MOFs can be quite high, with the insulin uniformly permeating to the center of the MOFs. For example, in some embodiments of the insulin-loaded MOFs, the insulin loading is at least 10 weight percent (wt. %). This includes embodiments of the insulin-loaded MOFs having an insulin loading of at least 30 wt. % and further includes embodiments of the insulin-loaded MOFs having an insulin loading of at least 40 wt. %.

Insulin can be loaded into the MOFs by exposing the MOFs to an aqueous insulin solution for a time sufficient to allow the insulin to diffuse into the pores of the MOF. This process can be carried out at room temperature (e.g., ~23° C.), and a high insulin loading can be achieved in a short time. For example, as illustrated in the Example, loadings of greater than 35 wt. % can be achieved in a period of 1 hour or less.

Once the insulin-loaded MOFs have been formed, they can be isolated from solution using, for example, filtration and/or centrifugation and can optionally be washed and allowed to dry. Then they can be formulated into a liquid or solid oral dosage form, such as a tablet containing the insulin-loaded MOFs with or without suitable diluents that is designed to disintegrate in a physiological environment. An effective amount of the insulin-loaded MOFs may be administered to a patient. An effective amount of an insulin-loaded MOF refers to an amount that improves a condition related to an insulin deficiency (e.g., diabetes) in the patient. By way of illustration only, effective amounts of the MOFs can include doses in the range from about 50 mL to 200 International Units (IU) per mL. The patient may be an animal, more specifically a mammal, such as a human.

In order to facilitate the internalization of the insulin-loaded MOFs by biological cells, the MOFs can be functionalized by oligonucleotides and, in particular, with terminal phosphate-modified DNA, to render them more colloidally stable in a physiological environment. This is illustrated in Example 3. By functionalizing the surfaces of insulin-loaded MOFs with oligonucleotides, cellular uptake can be increased, relative to the uptake of the native insulin, thereby providing a high payload with negligible cytotoxicity.

EXAMPLES

Figure 1A:
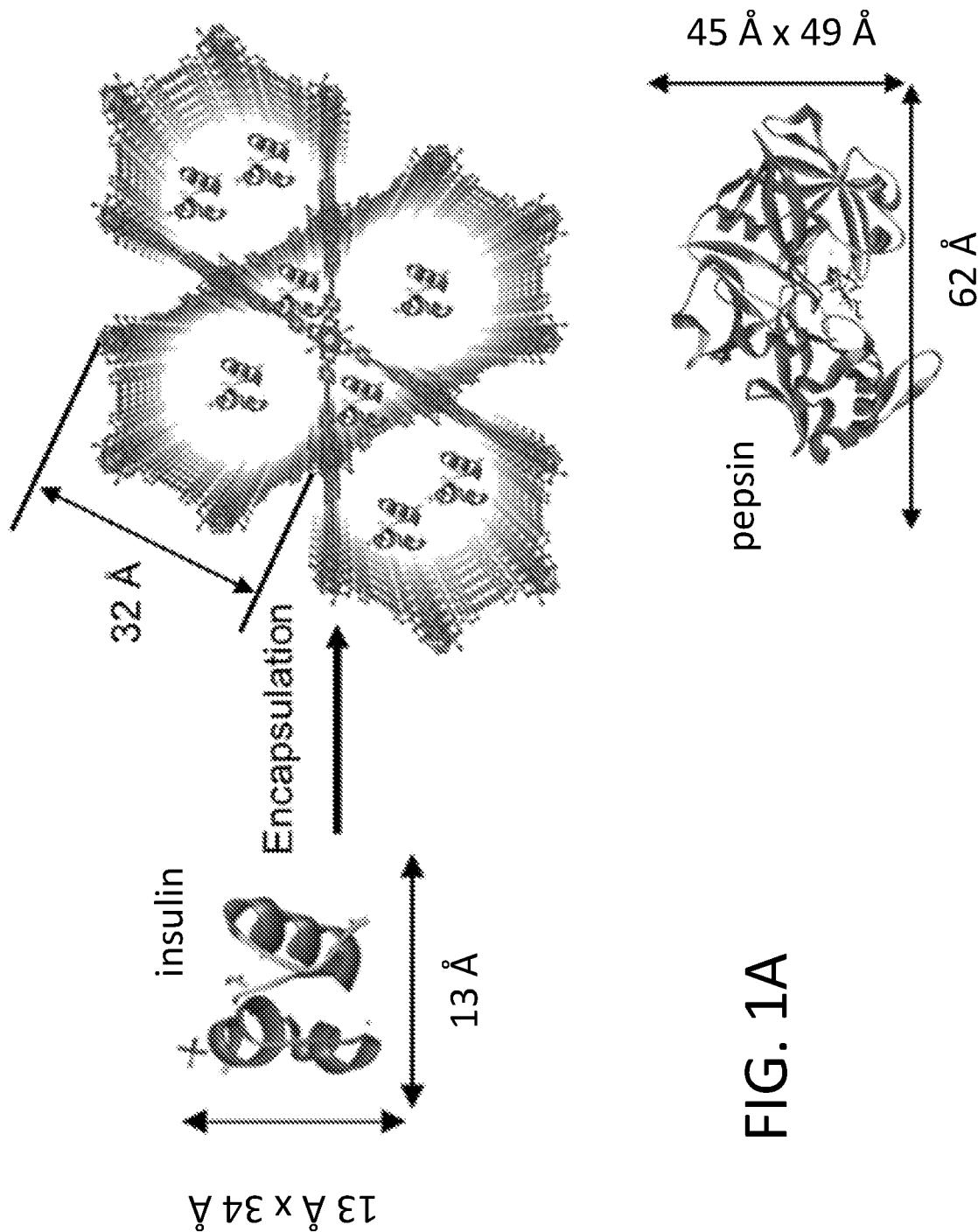
FIG. 1B is a schematic representation of exposure of free insulin and insulin@NU-1000 to stomach acid. Free insulin denatures in stomach acid and is digested by pepsin. Insulin@NU-1000 releases insulin when exposed to a phosphate buffered saline (PBS)
Figure 1B:
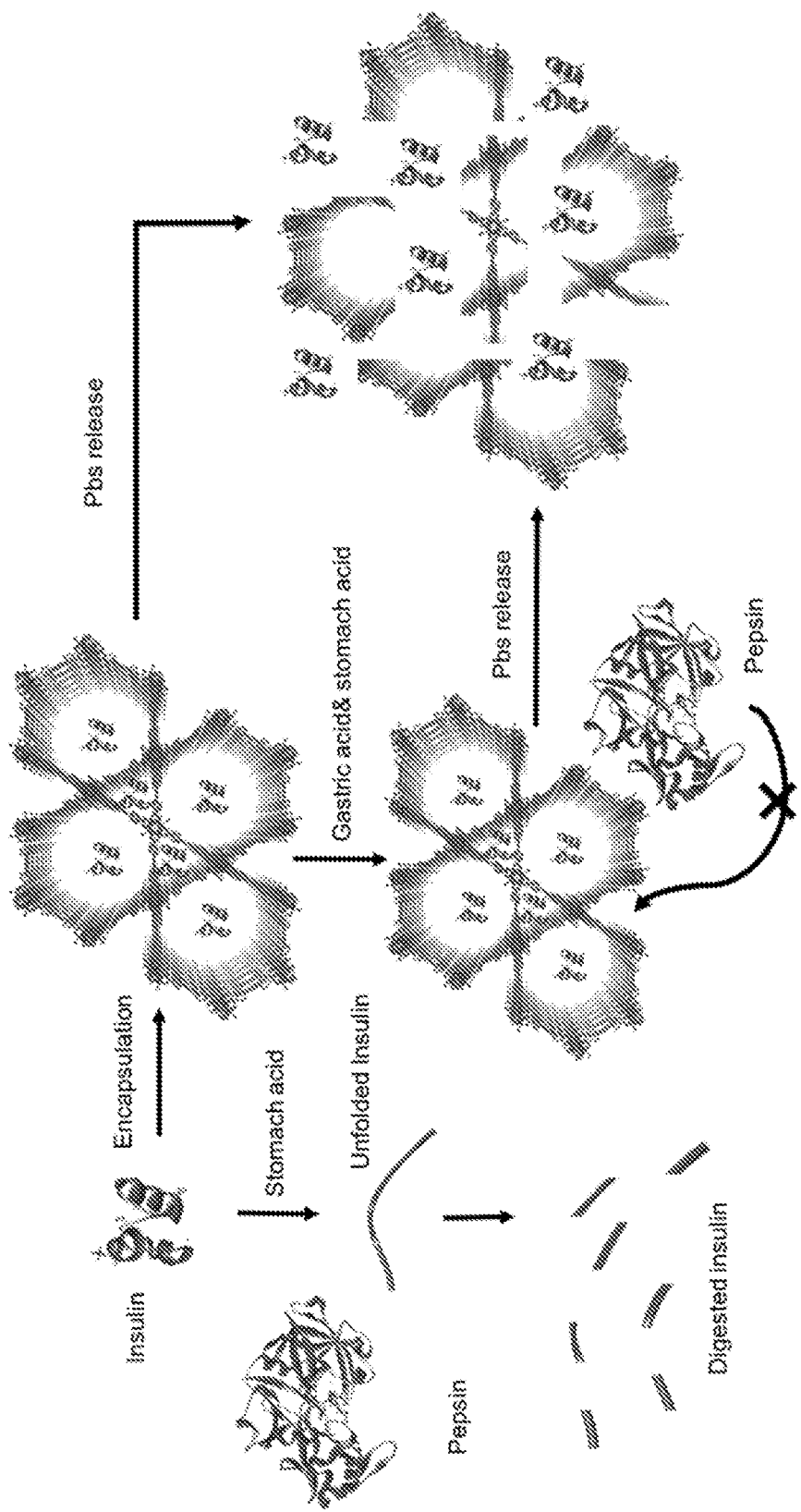

Example 1. This example demonstrates that NU-1000 satisfies the key requirements of an insulin delivery agent, namely sufficient porosity, favorable interactions, protection of insulin in harsh environments, and controlled insulin release. The one-dimensional pores of NU-1000 (mesopores with size ~30 Å and micropores with size ~12 Å in diameter) are ideally sized to not only allow insulin (13 Å×13 Å) to diffuse through the framework (FIG. 1A), but to also exclude pepsin (48 Å×64 Å), thereby limiting its proteolysis. Insulin molecules can be adsorbed by NU-1000 crystals because of the electrostatic interaction between insulin molecules and NU-1000 during the adsorption and their hydrophobicity, as illustrated by the zeta potential measurements shown in FIG. 9. When in acidic environments like the stomach, confinement within the pores inhibits excessive insulin unfolding and significantly reduces degradation (FIG. 1B). Under simulated bloodstream conditions, which are high in phosphate ions, NU-1000 will slowly degrade and release the encapsulated insulin (FIG. 1B). Here, a route to encapsulate and stabilize insulin in NU-1000 is reported, and a controlled release from the composite and post-release activity is demonstrated.

NU-1000 was synthesized and activated according to a reported procedure, and the size distribution was tested with Dynamic Light Scattering (DLS). Size distribution was performed to determine the average size (FIG. 10). (Wang, T. C., et al., *Nat. protoc.* 2016, 11, 149.) MOF crystals were soaked in an insulin solution ($4 \times 10^{-4}$ g/L in deionized (DI) water at pH 4) for 30 minutes at room temperature to encapsulate the insulin. The resulting solid composite, insulin@NU-1000, was isolated by filtration and washed with DI water to remove excess insulin. By the following protocol, dye-labeled insulin (AlexaFluor-647) was encapsulated in NU-1000, and its uptake was observed by in situ confocal laser scanning microscopy (CLSM) and quantified by monitoring the concentration of insulin in the supernatant by UV-vis spectroscopy. The highest loading was achieved after the MOF was exposed to the insulin solution for 3 hours (FIG. 2A), and the percentage of labeled insulin adsorbed with time was monitored (FIG. 2B). Inductively coupled plasma-optical emission spectroscopy (ICP-OES) was used to determine the S (3 disulfide bonds per insulin molecule) to Zr (from NU-1000) ratio for insulin@NU-1000, and the thermogravimetric analysis (TGA) results matched with the insulin loading (FIG. 11). NU-1000 exhibited a loading capacity about 40 wt. %.

The insulin@NU-1000 material was fully characterized via nitrogen adsorption/desorption measurements, PXRD, and scanning electron microscopy (SEM). As expected, the $N_2$ isotherm indicated that insulin@NU-1000 had a lower $N_2$ uptake capacity and therefore lower surface area than the parent NU-1000 (FIG. 3A). Further, the DFT calculated pore size distribution revealed a significant reduction of the hexagonal mesopore volume and a smaller, but still ample, decrease for the triangular micropore volume (FIG. 3B). This suggests that insulin resided in both pores. PXRD patterns and SEM images verify that NU-1000 retained its crystallinity even after encapsulation of insulin (FIG. 3C). Furthermore, SEM dispersive X-ray spectroscopy (SEM-EDX) indicated that insulin was uniformly distributed throughout NU-1000 crystals (FIG. 3D).

While high loading capacities are desirable, it is also vital that the delivery agent effectively protects insulin from harsh conditions and releases the insulin only in the target biological environment. The insulin release process was examined by exposing insulin@NU-1000 samples to solutions designed to emulate conditions that an orally delivered insulin drug may encounter. Specifically, samples were exposed for 1 hour to one of the following: HCl solution (pH=1.29) simulating the stomach pH, or phosphate-buffered saline (PBS) solution (pH=7.4) mimicking the blood stream (FIG. 4A). The amount of insulin released was again quantified by analyzing the concentration of labeled insulin in the supernatant by UV-vis spectroscopy after exposure to the aforementioned conditions. In a simulated stomach acid solution (pH=1.29), no insulin was found to leach from insulin@NU-1000 for at least 30 minutes. This suggests that insulin encapsulated in NU-1000 is protected from denaturation in the harsh conditions of the stomach. Additionally, after only 20 minutes of exposure to the PBS solution, NU-1000 degradation afforded the release of insulin. After 1 hour, the encapsulated insulin was entirely released from insulin@NU-1000. The degradation of NU-1000 crystals was monitored by using UV-vis spectroscopy to determine the concentration of linker in the supernatant. In a simulated stomach acid environment, NU-1000 crystals remained stable for 1 hour. On the contrary, in PBS, NU-1000 started to degrade after 10 minutes, and the degradation percentage reached around 10% of total insulin crystals in 1 hour. These results demonstrate that insulin is protected in environments mimicking the stomach and released in those designed to imitate the bloodstream, the target delivery point.

Considering insulin is only an effective therapeutic agent when in its active form (i.e. not denatured or digested), an enzyme-linked immunosorbent assay (ELISA) was employed to determine the concentration of active insulin after release from the framework and to further evaluate the effect of release conditions on insulin activity (FIG. 4B). The initially encapsulated insulin was assumed to be entirely active prior to release from insulin@NU-1000. As expected, free insulin exposed to stomach acid lost the entirety of its activity, confirming the necessity of an encapsulation method if insulin must pass through the stomach. When insulin@NU-1000 was exposed to PBS, the released protein retained its full activity. Further, insulin released from insulin@NU-1000 samples first exposed to gastric acid or stomach acid solutions followed by exposure to a PBS solution also retained the vast majority of its activity (92% for gastric acid and 77% for stomach acid). This suggests that insulin@NU-1000 can withstand the low pH environment of the stomach and release insulin in the desired environment. The high retention of insulin activity even after exposure to such harsh conditions further demonstrates the ability of NU-1000 to protect insulin. NU-1000 stabilizes and protects insulin under denaturing conditions encountered in the stomach (gastric acid or stomach acid solutions) and releases the encapsulated insulin under conditions mimicking the delivery target point, the bloodstream (PBS solution).

Materials and Methods

Materials. Human recombinant insulin (molecular formula: $C_{257}H_{383}N_{65}O_{77}S_6$, molecular weight: 5807.57, catalog number: 91077C-100MG) was produced from Sigma-Aldrich, USA. Insulin, Alexa fluor 647 labeled Insulin (human), was purchased from NanoCS, USA. An ELISA kit was purchased from Fisher Scientific, USA. A batch of 2.5 g MOF NU-1000 was synthesized following the published procedure. (Wang et al., 2016) The sodium chloride, potassium chloride, disodium phosphate, and monopotassium phosphate used to make phosphate-buffered saline (PBS) were provided by Sigma-Aldrich.

Physical methods and measurements. Inductively coupled plasma-optical emission spectroscopy (ICP-OES) was used to test the ratio of Zr (Zr nodes in NU-1000) to S (disulfide bonds in insulin) in an insulin@NU-1000 sample to confirm the highest loading of insulin in NU-1000. The experiment was performed on a computer-controlled (QTEGRA software v. 2.2) Thermo iCap 7600 Duo ICP-OES (Thermo Fisher Scientific, Waltham, Mass., USA) operating in standard mode. The insulin@NU-1000 samples (2-3 mg) were digested by an acidic solution ($vHNO_3$:$vH_2O_2$=3:1) by heating in a Biotage (Uppsala, Sweden) SPX microwave reactor (software version 2.3, build 6250) at 150° C. for 5 minutes. The solution was then diluted by Millipore water and analyzed for S and Zr content compared to the standard S and Zr solutions. $N_2$ sorption isotherm measurements were performed on a Micromeritics Tristar II 3020 (Micromeritics, Norcross, Ga.) at 77 K. Between 30 and 50 mg of material was used for each measurement. PXRD data were collected on a Rigaku model ATX-G diffractometer equipped with a Cu rotating anode X-ray source. SEM images and energy dispersive spectroscopy (EDX) profiles were collected on a Hitachi SU8030. Samples were coated with $OsO_4$ to ~7 nm thickness in a Denton Desk III TSC Sputter Coater (Moorestown, N.J.) before SEM-EDX analysis. CLSM was performed on 10 μm-long NU-1000 crystals to examine the distribution of AlexaFluor-647 dye-labeled insulins throughout the matrix. Fluorescence was examined, applying CLSM on a Leica TCS SP5. The Ar laser was set to 5%. Bit depth was set to 12 to achieve 4096 grey levels intensity resolution. Laser line 633 with 3% laser power was used to visualize AlexaFluor-647 dye-labeled insulins on NU-1000 at different depths along the z direction. An ELISA test for the insulin activity was performed following the manual in the ELISA Insulin Kit, and the results were determined by UV-vis.

Zeta Potential and DLS Size Distribution

Samples were made up in a $10^{-3}$ 1×Tris buffer at a concentration of 0.1 mg/mL and sonicated for 15 minutes. The pH from 1 to 7 of the solution was manually adjusted by the addition of gastric acid to 10-15 mL of the suspension before the zeta potential and DLS size distribution were measured.

Insulin Encapsulation

Insulin encapsulation with NU-1000. 3 mg of activated NU-1000 crystals were treated with insulin solution (in DI water, $4\times10^{-4}$ g/L) for 1 hour at room temperature to encapsulate insulin. Insulin loading was measured by ICP-OES and TGA. To remove the insulin attached to the surface of NU-1000, the supernatant was decanted, and the solid sample was then washed with DI water three times to remove the insulin molecules attached to the surface of the crystals. Insulin loading was calculated by:

$$\text{loading} = \frac{\text{weight of encapsulated insulin molecules}}{\text{weight of the encapsulating material}} \times 100\%.$$

TGA. TGA was performed on a TGA/DCS 1 system (Mettler-Toledo AG, Schwerzenbach, Switzerland), which runs on a PC with STARe software. Samples were heated from 25 to 600° C. at a rate of 10° C./min under flowing $N_2$. The elemental analysis was performed by Galbraith laboratories, Inc. (Knoxville, Tenn.).

The loading of insulin@NU-1000 was calculated with the following method:

$$\text{loading} = \frac{28\%}{72\%} \times 100\% = 38.9\%.$$

Insulin647 encapsulation with NU-1000. 3 mg of activated NU-1000 crystals were treated with labeled insulin solution (in DI water, 1 mg/mL) for 1 hour at room temperature to encapsulate insulin. Insulin loading was monitored by testing the concentration of labeled insulin through UV-vis.

Confocal laser scanning microscopy experiments. CLSM was performed on 10 μm NU-1000 crystals to examine the distribution of insulin throughout the matrix.

Example 2. This example describes methods of synthesizing MOFs NU-1000, NU-1003, NU-1004, NU-1005, and NU-1006, which can be loaded with insulin using the procedures described in Example 1. The synthesis of a sixth MOF, NU-1007, is also described. This MOF could also be used for the loading and delivery of insulin. However, due to its larger hexagonal pore size (see WO 2017/21387), it would not be effective at discriminating against pepsin enzymes.

General Procedure for Csq-Net MOF Synthesis.

A stock solution of $ZrOCl_2 \cdot 8H_2O$ (200 mg, 0.62 mmol), TFA (750 μL, 10 mmol) and DMF (50 mL) were added into a 250 mL bottle. The solution was heated at 80° C. for 1 h and then allowed to cool down to room temperature. Ligands (L1-L6, 3040 mg, 0.03 mmol) in DMF (50 mL) were added to the 250 mL bottle to form a clear solution. The reaction mixture was placed in an oven at 100° C. for 3 h during which time a light-yellow suspension was formed.

Synthesis of Linkers.

Compounds L2 and L5 were prepared according to literature procedures. (Li, P. et al. Nanosizing a Metal-Organic Framework Enzyme Carrier for Accelerating Nerve Agent Hydrolysis. *ACS nano* 10, 9174-9182 (2016); and Wang, T. C. et al. Ultrahigh surface area zirconium MOFs and insights into the applicability of the BET theory. *J. Am. Chem. Soc.* 137, 3585-3591 (2015).) All reactions for the synthesis of ligands L2-L5 were performed in oven-dried round bottom flasks, fitted with rubber septa and reactions were conducted under a positive pressure of nitrogen, unless otherwise noted. Anhydrous and anaerobic solvents were obtained from a Schlenk manifold with purification columns packed with activated alumina and supported copper catalyst (Glass Contour, Irvine, Calif.). Stainless steel syringes were used to transfer air- and moisture-sensitive liquids. Thin layer chromatography (TLC) was performed on silica gel 60 F254 (E. Merck). Automated flash chromatography was performed on a Teledyne ISCO Combiflash RF using Redisep RF silica gel columns.

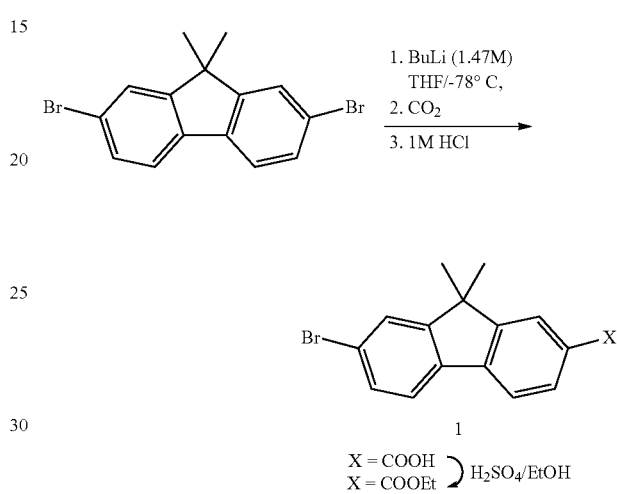

Ethyl 7-bromo-9,9-dimethyl-9H-fluorene-2-carboxylate (1): A 500 mL Schlenk flask was charged with 2,7-dibromo-9,9-dimethyl-9H-fluorene (10.56 g, 30 mmol) and 250 mL anhydrous THF. The solution was cooled down to −78° C. and n-BuLi (1.47 M, 20.4 mL, 30 mmol) was added dropwise. After stirring for 3 h, $CO_2$ to bubbled into the solution, and the reaction was warmed to room temperature overnight. The reaction mixture was then diluted with diethyl ether, and extracted with water 3×. 1 M aq. HCl was added to the combined aqueous layers and stirred for 2 h, during which a white precipitate formed. The white solid (7.95 g) was collected by vacuum filtration, dried under vacuum, and used without further purification. In a 250 mL round bottom flask, a suspension of the white solid, 2-3 mL conc. $H_2SO_4$, and 100 mL EtOH was refluxed for 6 h. After cooling down to room temperature, the reaction was diluted with 1 M aq NaOH, then extracted with EtOAc 3×. The organic layers were combined, dried over $MgSO_4$, then concentrated under reduced pressure. The residue was purified by flash chromatography using a gradient from 100% hexanes to 5% ethyl acetate in hexanes to yield a white solid (7.04 g, 68% yield).

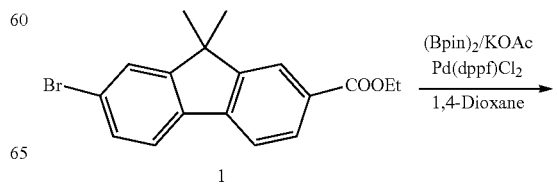

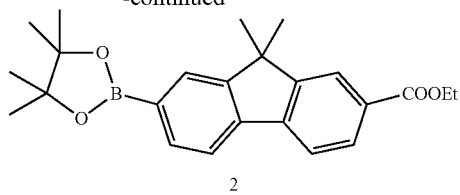

Ethyl 9,9-dimethyl-7-(4,4,5,5-tetramethyl-1,3,2-dioxaborolan-2-yl)-9H-fluorene-2-carboxylate (2): In a 150 mL 2-neck flask, 1 (1.04 g, 3.0 mmol), KOAc (0.88 g, 9.0 mmol), bis(pinacolato)diboron (1.52 g, 6.0 mmol), and 60 mL anhydrous 1,4-dioxane was degassed under $N_2$ for 30 min. Pd(dppf)Cl$_2$ (0.11 g, 0.15 mmol) was added to the reaction under positive $N_2$ flow, and the mixture was further degassed for 15 min. The reaction was refluxed under $N_2$ for 16 h, and after cooling down to room temperature the resulting black mixture was filtered through celite. The solvent was concentrated under reduced pressure, and the crude material was purified by flash chromatography using a gradient from 100% hexanes to 5% ethyl acetate in hexanes to yield a white solid (1.02 g, 87% yield).

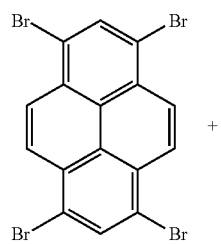

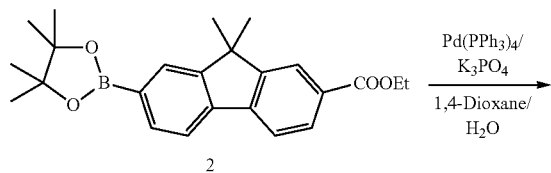

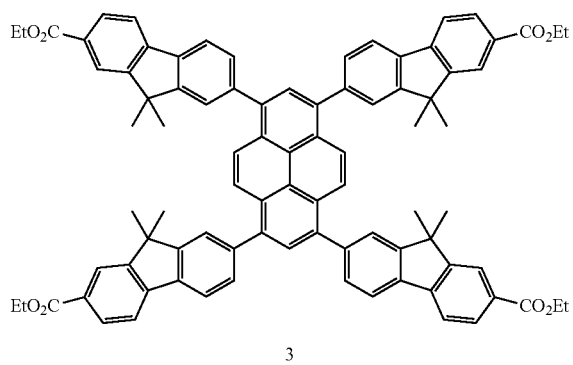

Tetraethyl 7,7',7'',7'''-(pyrene-1,3,6,8-tetrayl) tetrakis (9,9-dimethyl-9H-fluorene-2-carboxylate) (3): In a 50 mL 2-neck flask, a suspension of 1,3,6,8-tetrabromopyrene (0.20 g, 0.38 mmol), 2 (0.68 g, 1.74 mmol), K$_3$PO$_4$ (1.5 M aq, 2 mL), and 20 mL 1,4-dioxane was degassed under $N_2$ for 30 min. Pd(PPh$_3$)$_4$ (22 mg, 0.02 mmol) was added to the reaction under positive $N_2$ flow, and the mixture was further degassed for 15 min. The reaction was refluxed under $N_2$ for 2 days, and after cooling down to room temperature the mixture was diluted with 10 mL H$_2$O. The yellow precipitate was filtered and thoroughly washed with water and acetone, then dissolved in hot chloroform and triturated with methanol. The bright yellow solid was collected and dried under vacuum (0.31 g, 64% yield).

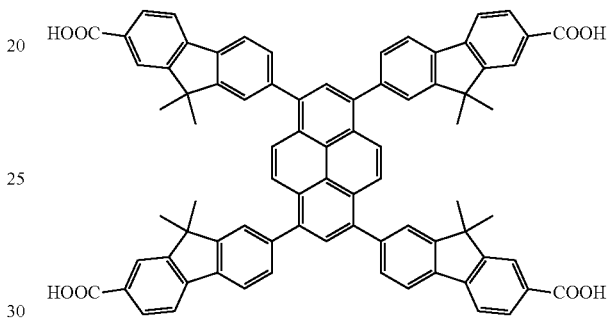

7,7',7'',7'''-(pyrene-1,3,6,8-tetrayl)tetrakis(9,9-dimethyl-9H-fluorene-2-carboxylic acid) (L3): A 200 mL round-bottom flask was charged with 3 (252 mg, 0.2 mmol), KOH (0.1 M aq, 25 mL), and 50 mL 1,4-dioxane. The suspension was refluxed overnight until a clear yellow solution was obtained. The reaction was cooled to 0° C. in an ice bath, and HCl was added dropwise to give a yellow precipitate, which was washed with water, dried, then redissolved in DMF and triturated with ether to give a bright yellow solid (189 mg, 82% yield).

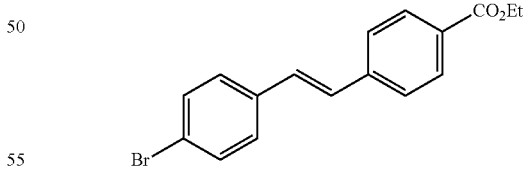

(E)-ethyl 4-(4-bromostyryl)benzoate (4): In a 250 mL round bottom flask, a suspension of 4'-bromostilbene-4-carboxylic acid (1.00 g, 3.3 mmol), 2-3 mL conc. H$_2$SO$_4$, and 100 mL EtOH was refluxed for 6 h. After cooling down to room temperature, the reaction was diluted with 1 M aq NaOH, then extracted with EtOAc 3×. The organic layers were combined, dried over MgSO$_4$, then concentrated under reduced pressure to give a white solid (1.02 g, quant.).

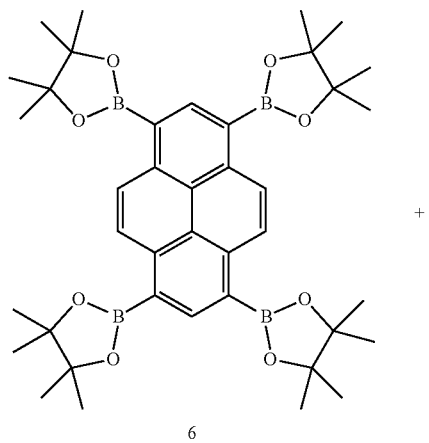

6

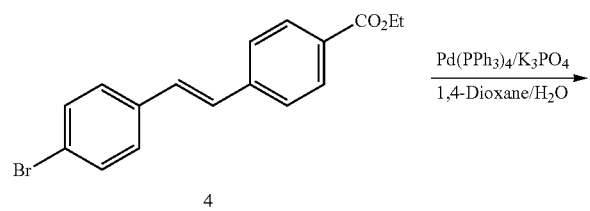

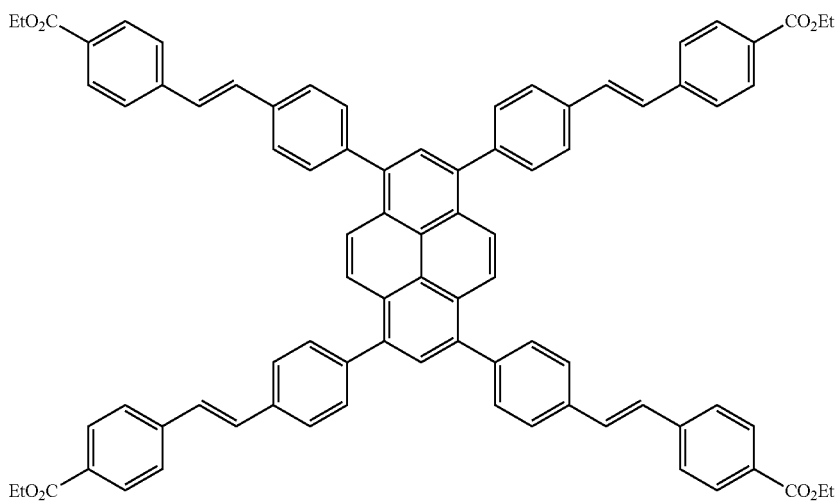

5

Tetraethyl 4,4',4'',4'''-((1E,1'E,1''E,1'''E)-(pyrene-1,3,6,8-tetrayltetrakis(benzene-4,1-diyl)) tetrakis(ethene-2,1-diyl)) tetrabenzoate (5): 1,3,6,8-tetrakis (4,4,5,5-tetramethyl-1,3,2-dioxaborolan-2-yl)pyrene (6) was synthesized according to literature procedure. (Sprick, R. S. et al. Tunable organic photocatalysts for visible-light-driven hydrogen evolution. *J. Am. Chem. Soc.* 137, 3265-3270 (2015).) In a 50 mL 2-neck flask, a suspension of 6 (226 mg, 0.32 mmol), 4 (478 mg, 1.44 mmol), $K_3PO_4$ (1.5 M aq, 2 mL), and 20 mL 1,4-dioxane was degassed under $N_2$ for 30 min. $Pd(PPh_3)_4$ (37 mg, 0.03 mmol) was added to the reaction under positive $N_2$ flow, and the mixture was further degassed for 15 min. The reaction was refluxed under $N_2$ for 2 days, and after cooling down to room temperature the mixture was diluted with 10 mL $H_2O$. The yellow precipitate was filtered and thoroughly washed with water and acetone, then dissolved in hot chloroform and triturated with methanol. The bright yellow solid was collected and dried under vacuum (223 mg, 58% yield).

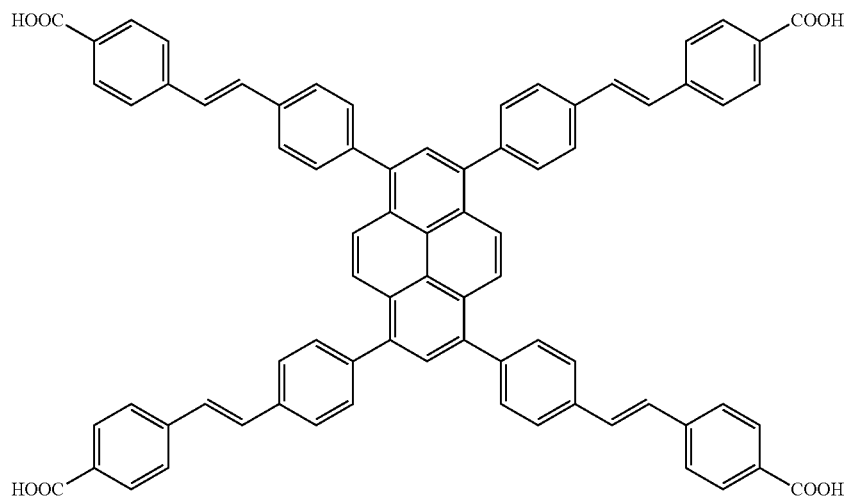 [SMILES: O=C(O)c1ccc(/C=C/c2ccc(-c3cc(-c4ccc(/C=C/c5ccc(C(=O)O)cc5)cc4)c4ccc5c(-c6ccc(/C=C/c7ccc(C(=O)O)cc7)cc6)cc(-c6ccc(/C=C/c7ccc(C(=O)O)cc7)cc6)c6ccc3c4c65)cc2)cc1]

4,4',4'',4'''-((1E,1'E,1''E,1'''E)-(pyrene-1,3,6,8-tetrayltetrakis(benzene-4,1-diyl))tetrakis(ethene-2,1-diyl))tetrabenzoic acid (L4): The title compound was prepared ESI-HRMS calculated [M-H]⁻ for $[C_{76}H_{49}O_8]^-$ is 1089.3433, found 1089.3393.

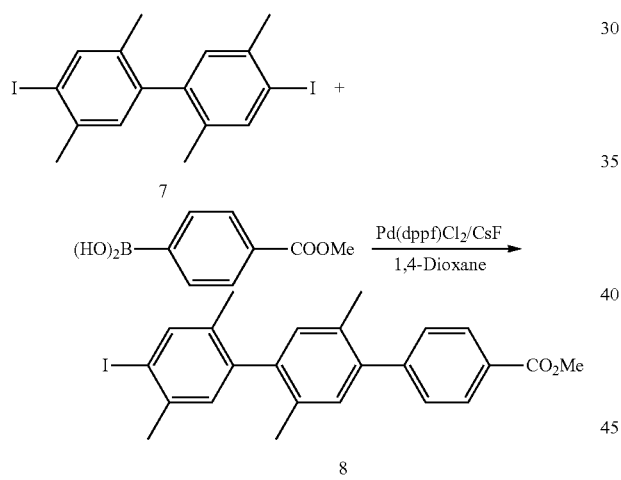

Methyl 4''-iodo-2',2'',5',5''-tetramethyl-[1,1':4',1''-terphenyl]-4-carboxylate (8): 4,4'-diiodo-2,2',5,5'-tetramethyl-1,1'-biphenyl (7) was synthesized according to literature procedure. (Grunder, S. et al. Molecular gauge blocks for building on the nanoscale. Chem. Eur. J. 18, 15632-15649 (2012).) A mixture of (4-(methoxycarbonyl)phenyl)boronic acid (360 mg, 2.0 mmol), 7 (3.69 g, 8.0 mmol), CsF (911 mg, 6.0 mmol), and 150 mL 1,4-dioxane was degassed under $N_2$ for 30 min. Pd(dppf)Cl$_2$ (73 mg, 0.1 mmol) was added to the reaction under positive $N_2$ flow, and the mixture was further degassed for 15 min. The reaction was refluxed under $N_2$ for 12 h, and after cooling down to room temperature the mixture was diluted with $H_2O$ and extracted with DCM 3×. The organic layers were combined, dried over MgSO$_4$, then concentrated under reduced pressure. The residue was purified by flash chromatography using a gradient from 100% hexanes to 10% ethyl acetate in hexanes to yield a white solid (489 mg, 52% yield).

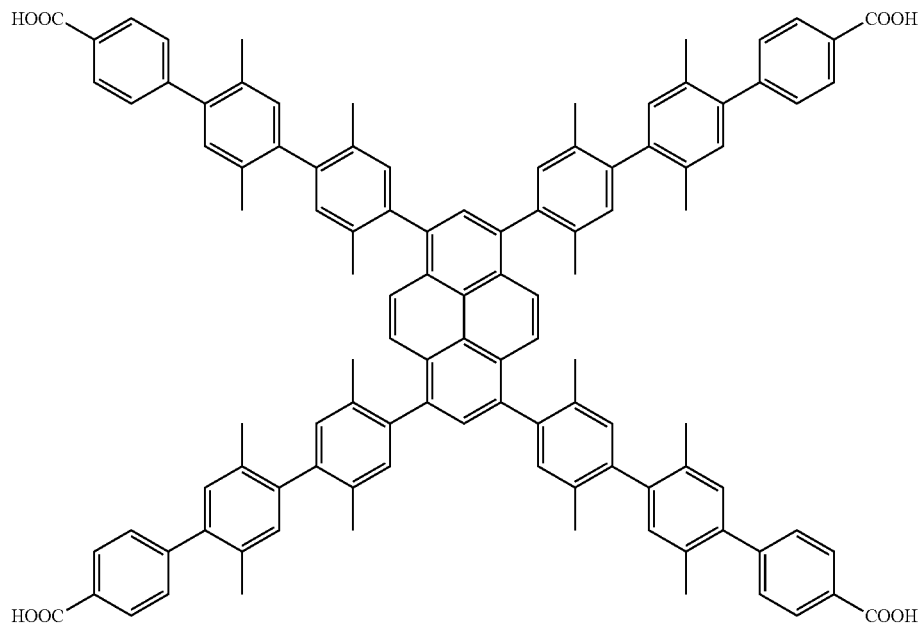 [SMILES: Cc1cc(-c2cc(C)c(-c3cc(-c4cc(C)c(-c5cc(C)c(-c6ccc(C(=O)O)cc6)cc5C)cc4C)c4ccc5c(-c6cc(C)c(-c7cc(C)c(-c8ccc(C(=O)O)cc8)cc7C)cc6C)cc(-c6cc(C)c(-c7cc(C)c(-c8ccc(C(=O)O)cc8)cc7C)cc6C)c6ccc3c4c65)cc2C)c(C)cc1-c1ccc(C(=O)O)cc1]

4',4''',4''''',4'''''''-(pyrene-1,3,6,8-tetrayl)tetrakis(2',2'',5',5''-tetramethyl-[1,1':4',1''-terphenyl]-4-carboxylic acid) (L6): The title compound was prepared in the same procedure as L4, using 6 and 8 for Suzuki coupling and subsequent acid hydrolysis, yielding an off-white solid (174 mg, 51% yield over two steps).

Example 3. This example illustrates a new method for the intracellular delivery of proteins that relies on nucleic acid-MOF NP conjugates (FIG. 13A). In this protocol, two water stable zirconium mesoporous MOFs, NU-1000 ($Zr_6(\mu_3-O)_4(\mu_3-OH)_4(OH)_4(H_2O)_4(TBAPy)_2$, $H_4$-TBAPy=4,4',4'',4'''-(porphine-5,10,15,20-tetrayl)tetrakis(benzoic acid)) and PCN-222/MOF-545 ($Zr_6(\mu_3-O)_4(\mu_3-OH)_4(OH)_4(H_2O)_4(TCPP-H_2)_2$, $H_4$-TCPP-$H_2$=tetrakis(4-carboxyphenyl)porphyrin), were synthesized in nanoparticle form and used to encapsulate insulin, (FIG. 13B) as described in Example 1. Next, these insulin@MOF NPs were surface functionalized with terminal phosphate-modified DNA to yield insulin@DNA-MOF NPs (FIG. 13C). (Morris, W., et al., *J. Am. Chem. Soc.* 2014, 136, 7261-7264.) The 3D oligonucleotide shell creates a steric and electrostatic barrier to stabilize MOF NPs in high dielectric media and renders them functional with respect to cellular entry. (Wang, S., et al., *J. Am. Chem. Soc.* 2017, 139, 9827-9830.) In principle, this strategy can be generalized to MOFs with different pore sizes and topologies, thereby creating an arsenal of nucleic acid-MOF-based delivery vehicles for transporting functional enzymes across cellular membranes with high payloads.

NU-1000 MOF NPs [180(20)×70(10) nm] were synthesized via a solvothermal reaction of zirconium chloride ($ZrCl_4$) with $H_4$-TBAPy ligands, modulated by acetic acid in N,N-Dimethylformamide (DMF) at 90° C. Similarly, PCN-222 NPs [210(30)×50(10) nm] were synthesized via a solvothermal reaction between zirconyl chloride octahydrate ($ZrOCl_2 \cdot 8H_2O$) and $H_4$-TCPP-$H_2$ ligands, modulated by dichloroacetic acid in DMF at 130° C. Next, the thermally activated crystals of NU-1000 were treated with a bis-tris-propane buffer (BTP, pH=7) solution of insulin (0.4 mg/mL). The MOF NP insulin encapsulation efficiencies were determined by measuring the S [for insulin] and Zr (for MOFs) contents by inductively coupled plasma-optical emission spectroscopy. The maximum insulin loadings of 34 and 63 wt % were determined for NU-1000 and PCN-222 NPs, respectively, which are consistent with those reported in Example 1. The excess insulin in the supernatant was removed by sequential washing steps with DI water.

The insulin@MOF NPs were functionalized with nucleic acids by coordinating the terminal phosphate-modified oligonucleotides to the surface Zr SBUs. The sequence used here, 5' $(dGGT)_{10}$-phosphate 3' (SEQ ID NO: 1), was chosen because it is known with SNAs that a G-rich shell, relative to poly dT shells, facilitates higher cellular uptake. In a typical NP functionalization experiment, excess oligonucleotides were added to a colloidal dispersion of MOF NPs and incubated for 4 hours. Particle DNA coverage was quantitatively determined by measuring the P to Zr ratio by ICP-OES (8±1 nmol/mg for NU-1000 NPs and 10±1 nmol/mg for PCN-222 NPs). Powder X-ray diffraction (PXRD) and scanning electron microscopy (SEM) confirmed that the crystallinity and morphologies of the MOF NPs were maintained, post-DNA functionalization. Importantly, dynamic light scattering (DLS) verified that DNA surface functionalization significantly increases MOF NP colloidal stability in cellular media (90% DMEM buffer+10% fetal bovine serum) for at least 24 hours. (FIGS. 14A and 14B).

In addition to colloidal stability, the intra- and extracellular stability of protein delivery vehicles in serum and serum free but biologically relevant matrices is important. Indeed, the ability to control degradation could be useful in the development of temporally-controlled drug delivery applications. Under physiological conditions, intracellular fluid exhibits significantly higher inorganic phosphate concentration (5-10 mM) as compared to that of serum (~1 mM). Therefore, the degradation profiles of insulin@DNA-NU-1000 NPs and insulin@DNA-PCN-222 NPs were evaluated by exposing them to solutions designed to emulate both extracellular and intracellular conditions. To simulate serum, MOF NPs were incubated with 90% DMEM buffer+ 10% blood serum (pH=7.0) at 37° C. with gentle shaking (400 rpm), where less than 5% of degradation occurred within 12 hours for both vehicles, and less than 20% within 96 hours, demonstrating DNA-MOF NPs exhibit excellent stability and should be compatible with blood (FIG. 15, dashed). In contrast, when the same MOF NPs were incubated in an intracellular medium simulant (1×phosphate buffered saline, pH=7.0) at 37° C. with gentle shaking, the particles degraded at much faster rates (FIG. 15, solid) due to the high phosphate content, which competitively binds to Zr clusters. Interestingly, DNA-PCN-222 NPs exhibit a faster degradation rate (half-life=1 h) when compared to that of DNA-NU-1000 NPs (half-life=40 h). Such degradation kinetics could be useful for in vivo purposes by providing a means to control the temporal release of proteins from particles, once inside cells.

To directly visualize nucleic acid-modified, insulin encapsulated MOF NPs, confocal laser scanning microscopy was used to image them. Due to the resolution limits of confocal microscopy, larger particles (2.8 µm×10 µm for NU-1000), AlexaFluor 647 dye (AF647)-labeled insulin, and TAMRA-labeled DNA were used. With such particles, the co-localization of AF647 and TAMRA signals can be clearly observed, verifying the encapsulation of insulin and DNA surface functionalization of the MOF. To obtain detailed information regarding relative distribution of insulin and DNA, Z-stack images of a single MOF particle were taken, where TAMRA signal (DNA) was observed to preferentially occupy the periphery while AF647 (insulin) was present throughout the particle. Brighter AF647 signals were observed at both ends of the particle as compared to the center section of the MOF, consistent with protein diffusion into NU-1000 through its ID channels. Due to the large diameter of the MOF pores (3.2 nm for NU-1000 and 3.7 nm for PCN-222), single stranded DNA was also expected to penetrate through the MOF pores and functionalize the internal surface, leading to fluorescence signal inside the particles. As verified by $N_2$ adsorption isotherms, reduced $N_2$ uptake capacity was observed post-insulin encapsulation for both MOFs, and further loss of porosity was observed post-DNA functionalization. Furthermore, an enzyme-linked immunosorbent assay (ELISA) was employed to determine whether insulin would leach from the MOF NP pores and/or lose catalytic activity during the DNA functionalization process. In both cases, no appreciable leaching and/or insulin activity loss was observed for insulin@DNA-NU-1000 and insulin@DNA-PCN-222 constructs.

A key characteristic of SNA-NP conjugates is their ability to effectively enter cells. Therefore, insulin@DNA-MOF NPs were tested to determine whether they exhibited enhanced cellular uptake. Specifically, NU-1000 and PCN-222 NPs were encapsulated with AF647-labeled insulin and functionalized with TAMRA-labeled DNA and incubated with human ovarian adenocarcinoma cells, SKOV-3, for 0.5 h, 2 h, 6 h, and 24 h. As a control group, a mixture of free TAMRA-labeled DNA and AF-647-labeled insulin was incubated with cells at the same concentration. Confocal laser scanning microscopy confirms the enrichment of insulin in cellular vesicles, as evidenced by strong colocalization of AF647 and TAMRA signals in cellular vesicles (FIG. 16A-FIG. 16C). The Z-stack images confirm that the insulin@DNA-MOF NPs are internalized by the cells, as opposed to attached to their membranes. Consistent with this conclusion, flow cytometry showed a 10-fold increase in fluorescence in cells treated with insulin@DNA-MOF NPs as compared to those treated with the free insulin+DNA control group (FIG. 16D). The insulin@DNA-MOF NPs exhibits similar levels of enhancement in cellular uptake, as compared to that of conventional SNA-NP conjugates. Finally, MTT assays show that the particles result in no apparent cytotoxicity or anti-proliferative effects (FIG. 16E).

Materials

All reagents, unless otherwise stated, were obtained from commercial sources and were used without further purification. Human recombinant insulin (molecular formula: $C_{257}H_{383}N_{65}O_{77}S_6$, molecular weight: 5807.57, catalog number: 91077C-100MG) was purchased from Sigma-Aldrich, USA. Insulin, Alexa fluor 647 labeled Insulin (human) was purchased from NanoCS, USA. ELISA kit was purchased from Fisher Scientific, USA. All oligonucleotides used in this work were synthesized on a solid-support MM12 synthesizer with reagents purchased from Glen Research. The water used in all experiments was ultrapure deionized (DI) grade (18.2 MO-cm resistivity), obtained from a Milli-Q Biocel system (Millipore, Billerica, Mass., USA).

Synthesis of 150 nm NU-1000 MOF NPs: 8 mg (34 µmol) of zirconium chloride and 2.0 mg (3.0 µmol) of 1,3,6,8-tetrakis(p-benzoic acid)pyrene ($H_4$TBAPy) ligand were dissolved in 2.0 mL of N,N-Dimethylformamide (DMF) and 0.4 ml acetic acid, to which 0.2 ml DI water was added. The solution vial was then placed in a 90° C. conventional oven and heated for 30 min, resulting in a light yellow suspension. After cooling down to room temperature, the nanocrystals were collected by centrifugation (15000 rpm, 30 min), followed by solvent exchange with DMF and acetone for three times, and subsequently activated with HCl.

Synthesis of 10 µm NU-1000 MOF particles: The synthesis of 10 m NU-1000 particles was based on a literature reported method. (Li, P., et al., *Chem. Commun.* 2015, 51, 10925-10928.) Briefly, in a 6-dram vial, 70 mg of $ZrCl_4$ (0.30 mmol) and 2.7 g (22 mmol) of benzoic acid were dissolved in 8.0 mL of N,N-Diethylformamide (DEF) with gentle sonication. The solution was incubated at 80° C. in an oven for 1 h. After cooling down to room temperature, 40 mg (60 µmol) of $H_4$TBAPy was added to this solution, and the mixture was sonicated for 20 min. The yellow suspension was next heated at 120° C. in an oven for 48 h. After cooling down to room temperature, the resulting yellow single crystals were solvent exchanged with DMF and acetone three times each and subsequently activated with HCl.

Synthesis of PCN-222 MOF NPs: PCN-222/MOF-545 nanocrystals (~200 nm in length) were synthesized following a literature reported method with minor modifications. (Kelty, M. L., et al., *Chem. Commun.* 2016, 52, 7854-7857.) Zirconyl chloride octahydrate (38 mg, 0.12 mmol) and tetrakis(4-carboxyphenyl)-porphyrin (6.5 mg, 8.2 µmol) were dissolved in 16.3 mL DMF in a 22 mL borosilicate vial with a Teflon-lined cap. Dichloroacetic acid (0.25 mL, 3.0 mmol) was added, and the resulting solution was heated at 130° C. for 18 hours to afford dark purple rod-shaped nanocrystals and a yellow mother liquor. The nanocrystals were collected by centrifugation (15000 rpm, 5 min), followed by solvent exchange with DMF three times.

Powder X-ray diffraction: The crystallinity of the MOF nanoparticles (as-synthesized, insulin encapsulated, and insulin encapsulated DNA-MOF conjugates) were confirmed by powder X-ray diffraction (PXRD). PXRD data were collected on a Rigaku model ATX-G diffractometer equipped with a Cu rotating anode X-ray source.

Insulin encapsulation: Insulin encapsulation was achieved by treating activated MOF nanoparticles (~3 mg) with a bis-tris-propane buffer (BTP, pH=7) solution of insulin (0.4 mg/mL) for 1 hour at room temperature. Insulin loading was measured by inductively coupled plasma-optical emission spectroscopy (ICP-OES) and thermogravimetric analyses (TGA) based on the methods reported in Example 1. To remove excess insulin in solution, the supernatant was decanted and the solid sample was washed with DI water three times.

DNA Synthesis and Functionalization

Synthesis of oligonucleotides: Oligonucleotides were synthesized using a Mermaid MM12 DNA synthesizer (Bio Automation) on a standard CPG solid phase support. All oligonucleotides were deprotected under conditions recommended by the manufacturer and purified by reverse phase high performance liquid chromatography (HPLC). Characterization and determination of concentrations were determined by matrix assisted laser desorption ionization (MALDI-TOF) mass spectrometry and UV-Vis spectroscopy, respectively.

TABLE 1

DNA sequences used in this study

| # | Sequence Name | Sequence |
|---|---|---|
| 1 | polyG | 5'-(dGGT)$_{10}$-phosphate-3'<br>(SEQ ID NO: 1) |
| 2 | polyG-dye | 5'-(Tamra-dT)-(dGGT)$_{10}$-phosphate-3'<br>(SEQ ID NO: 2) |

3' Phosphate refers to 3-(4,4'-Dimethoxytrityloxy)-2,2-(dicarboxymethylamido)propyl-1-O-succinoyl-long chain alkylamino-CPG (3'-CPR II CPG). Tamra-dT refers to 5'-Dimethoxytrityloxy-5-[N-((tetramethylrhodaminyl)-aminohexyl)-3-acrylimido]-2'-deoxyUridine-3'-[(2-cyanoethyl)-(N,N-diisopropyl)]-phosphoramidite (Tamra-dT).

DNA functionalization: MOF NPs were functionalized with DNA based on a previously reported method with minor modifications. (Wang, S., et al., 2017) In a typical DNA functionalization experiment, excess phosphate terminated nucleic acid (~100 nmol) was added to MOF NP colloids (~2 mg), and then left on a shaker to incubate for 4 hours. Excess oligonucleotides were removed by solvent exchange with DI water via centrifugation (3×10000 rpm, 15 min), and finally dispersed in water.

To directly visualize the aggregation of unmodified MOF NPs, a cryo-STEM image was taken for the insulin encapsulated PCN-222 NPs in cell medium. Specifically, 4 pL of MOF NP samples (incubated in cell medium for 12 h) were pipetted onto glow discharged lacey carbon 200 mesh Cu grids (EMS Cat. #LC200-CU-100), blotted for 5 s, and plunge-frozen in liquid ethane with an FEI Vitrobot Mark III The samples were then loaded into a Gatan 626.6 Cryo Transfer Holder kept at −165° C. and imaged in a Hitachi HD2300 cFEG STEM at 200 kV utilizing high angular annular dark field (HAADF) Z-contrast.

Confocal fluorescence microscopy: NU-1000 MOF microparticles (10 μm, encapsulated with AF647-insulin and functionalized with Tamra labeled DNA) were imaged with Z stack using confocal fluorescence microscopy (Zeiss LSM 800, 63×objective with excitation at 546 and 640 nm for Tamra and AF647, respectively).

Degradation Profiles of DNA-NU-1000 and DNA-PCN-222

Degradation profile in simulated extracellular matrices: To simulate intravascular and interstitial fluid, MOF NPs were incubated with DMEM buffer+blood serum (pH=7.0) at 37° C. with gentle shaking (400 rpm). Specifically, around 50 μg of DNA-NU-1000 and DNA-PCN-222 were first dispersed in 200 μL DI water to form the stock solution (0.25 mg/mL). Next, 7 identical samples containing 20 μL of the stock solution and 980 μL (DMEM buffer+blood serum solution) (pH=7.0) were mixed and incubated on a thermal shaker for 0.5, 1.5, 6, 12, 24, 48, and 72 h, respectively. At each time point, one sample was collected and centrifuged (15000 rpm, 15 min) to remove remaining MOF NPs. The UV-vis absorbance of supernatant was measured and the percentage of linker release over time was calculated based on the standard curves.

Degradation profile in simulated intracellular matrices: Similar procedure was followed to measure the degradation profiles of DNA-NU-1000 and DNA-PCN-222 in 1×PBS solution to simulate their degradation in intracellular matrices (pH=7.0, 100 mM NaCl).

Nitrogen sorption isotherm measurements: $N_2$ sorption isotherm measurements were performed on a Micromeritics Tristar II 3020 (Micromeritics, Norcross, Ga.) at 77 K. For each experiment, approximately 20 to 30 mg of sample was measured. Surface areas were estimated by applying the Brunauer-Emmett-Teller (BET) equation. T-plot internal and external surface areas were determined by the Harkins and Jura equation in the second linear regions of $N_2$ isotherms (0.26 $P/P_0$ to 1.0 $P/P_0$).

Cell Uptake Experiments and Cytotoxicity Evaluation

Cell culture and incubation: Human ovarian cancer cells SK-OV-3 (ATCC® HTB-77™) and mice melanoma cells B16-F10 (ATCC® CRL-6475) were incubated at 37° C. with 5% $CO_2$. The media used to incubate these two cell lines were McCoy's 5A medium (ATCC® 30-2007™) and Dulbecco's Modified Eagle's Medium (DMEM) (ATCC® 30-2002™) (containing 10% fetal bovine serum (FBS) and 1% antibiotics), representatively. Cells were passed every 2 or 3 days to get the acceptable confluence.

Cell imaging with confocal fluorescence microscopy: Confocal fluorescence microscopy was performed on a confocal laser microscope (Zeiss LSM 800) system to observe cell internalization of the insulin@DNA-MOF NPs. In a typical experiment, SKOV-3 cells were first plated in flourishes with 5×10$^4$ confluence, and then incubated with: 1) AF647Insulin@Tamra-DNA-NU-1000, 2) AF647Insulin@Tamra-DNA-PCN-222, and 3) linear Tamra-DNA and AF647 labeled insulin (control group) (concentration see Table 2). After 6 h, excess particles in medium were washed out and cells were fixed with 4% formaldehyde. Cell skeleton actin (F-actin) was stained with AlexaFluor 488 Phalloidin (ThermoFisher A12379).

TABLE 2

DNA and insulin concentration used in this study

| # | Description | DNA concentration | Insulin concentration |
|---|---|---|---|
| 1 | AF647Insulin@Tamra-DNA-NU-1000 | 100 nM | ~180 nM |
| 2 | AF647Insulin@Tamra-DNA-PCN-222 | 100 nM | ~140 nM |
| 3 | Tamra-DNA<br>AF647Insulin | 100 nM | 160 nM |

Cellular Uptake by flow cytometry: LSR-II flow cytometry was used to identify the cellular uptake of both oligonucleotide and insulin. Skov-3 cells (5×10$^5$ cells/mL) were first incubated in flow tubes and then treated with AF647Insulin@Tamra-DNA-MOF NPs and the control group (free insulin+free DNA) (Table 2) for 15 min and 2 h. Excess particles were then washed out and cells were fixed with 4% formaldehyde. Flow data were first gated by SSA and FSA parameter, and positive gating in each channel was based on negative controls.

MTT assay: The anti-proliferative effects of insulin@DNA-MOF constructs were evaluated by MTT assay. Specifically, B16-F10 cells were seeded in a 96-well cell culture plate in DMEM medium at a density of $5 \times 10^4$ cells/mL with 10% FBS and 5% $CO_2$ at 37° C. for 24 h. Next, the culture medium was replaced by 200 μL of DMEM medium containing samples at different concentrations (with non-labelled DNA and insulin) and cultured for 72 h. Then, 10 μL of 5 mg/mL MTT solution (10% SDS) was added to each cell well. The cells were further incubated for 4 h, followed by removal of the culture medium with MTT. Finally, 100 μL of 10% SDS was added and incubated overnight at 37° C. The absorbance of MTT at 492 nm was measured on an automatic ELISA analyzer (SPR-960), with a reference absorbance at 977 nm. Each experiment was conducted 3 times and the averaged data were presented.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalent.

What is claimed is:

1. An insulin-loaded metal-organic framework molecule comprising:

a porous, channel-type zirconium metal-organic framework molecule having a cube-and-square network (csq-net) topology and comprising eight $Zr_6$ nodes that are connected by organic linkers; and insulin molecules within pores of the zirconium metal-organic framework, wherein the diameters of the largest pores of the porous zirconium metal-organic framework molecule are no greater than 62 Å.

2. The insulin-loaded metal-organic framework molecule of claim 1 having an insulin loading of at least 30 wt. %.

3. The insulin-loaded metal-organic framework molecule of claim 1, wherein the largest pores of the porous zirconium metal-organic framework molecule are no greater than 50 Å.

4. The insulin-loaded metal-organic framework molecule of claim 1, wherein the largest pores of the porous zirconium metal-organic framework molecule have diameters in the range from 30 to 45 Å.

5. The insulin-loaded metal-organic framework molecule of claim 1, wherein the organic linkers are tetratopic linkers having a backbone comprising a pyrene group and side arms.

6. The insulin-loaded metal-organic framework molecule of claim 5, wherein the side arms comprise a benzene group.

7. The insulin-loaded metal-organic framework molecule of claim 5, wherein the side arms comprise a naphthalene group.

8. The insulin-loaded metal-organic framework molecule of claim 5, wherein the side arms comprise a fluorene group.

9. The insulin-loaded metal-organic framework molecule of claim 5, wherein the side arms comprise a stilbene group.

10. The insulin-loaded metal-organic framework molecule of claim 5, wherein the side arms comprise a diphenylacetate group.

11. The insulin-loaded metal-organic framework molecule of claim 1, wherein the organic linkers are tetratopic linkers comprising an ethene-1,1,2,2-tetrayl (tetrakis-((([1,1'-biphenyl]-4-carboxylic acid))) group.

12. The insulin-loaded metal-organic framework molecule of claim 1, wherein the organic linkers are tetratopic linkers having a backbone comprising a parylene group and side arms.

13. The insulin-loaded metal-organic framework molecule of claim 1, wherein the organic linkers are tetratopic linkers having a backbone comprising a porphyrin group and side arms.

14. The insulin-loaded metal-organic framework molecule of claim 1, wherein a surface for the metal-organic framework molecule is functionalized with oligonucleotides.

15. A pharmaceutical tablet comprising insulin-loaded metal-organic framework molecules, the insulin-loaded metal-organic framework molecules comprising: a porous, channel-type zirconium metal-organic framework molecule having a cube-and-square network (csq-net) topology and comprising eight $Zr_6$ nodes that are connected by organic linkers; and insulin molecules within pores of the zirconium metal-organic framework, wherein the diameters of the largest pores of the porous zirconium metal-organic framework molecules are no greater than 62 Å.

* * * * *